US009951389B2

(12) United States Patent
Bassett et al.

(10) Patent No.: US 9,951,389 B2
(45) Date of Patent: Apr. 24, 2018

(54) DIAGNOSTIC MARKERS FOR TREATING CELL PROLIFERATIVE DISORDERS WITH TELOMERASE INHIBITORS

(71) Applicant: Geron Corporation, Menlo Park, CA (US)

(72) Inventors: Ekaterina Bassett, Los Gatos, CA (US); Bart Burington, Oakland, CA (US); Hui Wang, Sunnyvale, CA (US); Kevin Eng, Mountain View, CA (US)

(73) Assignee: Geron Corporation, Menlo Park, CA (US)

( * ) Notice: Subject to any disclaimer, the term of this patent is extended or adjusted under 35 U.S.C. 154(b) by 0 days.

(21) Appl. No.: 14/928,993

(22) Filed: Oct. 30, 2015

(65) Prior Publication Data

US 2016/0177403 A1 Jun. 23, 2016

Related U.S. Application Data

(63) Continuation of application No. 13/802,035, filed on Mar. 13, 2013, now Pat. No. 9,200,327.

(60) Provisional application No. 61/732,263, filed on Nov. 30, 2012.

(51) Int. Cl.
*C12Q 1/68* (2006.01)

(52) U.S. Cl.
CPC ..... *C12Q 1/6886* (2013.01); *C12Q 2600/106* (2013.01); *C12Q 2600/156* (2013.01)

(58) Field of Classification Search
CPC ...................................................... C12Q 1/68
See application file for complete search history.

(56) References Cited

U.S. PATENT DOCUMENTS

| | | | |
|---|---|---|---|
| 5,489,508 A | 2/1996 | West et al. |
| 5,583,016 A | 12/1996 | Villeponteau et al. |
| 5,639,613 A | 6/1997 | Shay et al. |
| 5,645,986 A | 7/1997 | West et al. |
| 5,648,215 A | 7/1997 | West et al. |
| 5,686,245 A | 11/1997 | West et al. |
| 5,686,306 A | 11/1997 | West et al. |
| 5,693,474 A | 12/1997 | Shay et al. |
| 5,707,795 A | 1/1998 | West et al. |
| 5,741,677 A | 4/1998 | Kozlowski et al. |
| 5,776,679 A | 7/1998 | Villeponteau et al. |
| 5,830,644 A | 11/1998 | West et al. |
| 5,834,193 A | 11/1998 | Kozlowski et al. |
| 5,837,857 A | 11/1998 | Villeponteau et al. |
| 5,840,495 A | 11/1998 | West et al. |
| 5,958,680 A | 9/1999 | Villeponteau et al. |
| 5,972,605 A | 10/1999 | Villeponteau et al. |
| 5,989,807 A | 11/1999 | West et al. |
| 6,007,989 A | 12/1999 | West et al. |
| 6,054,575 A | 4/2000 | Villeponteau et al. |
| 6,194,206 B1 | 2/2001 | West et al. |
| 6,258,535 B1 | 7/2001 | Villeponteau et al. |
| 6,320,039 B1 | 11/2001 | Villeponteau et al. |
| 6,368,789 B1 | 4/2002 | West et al. |
| 6,391,554 B1 | 5/2002 | West et al. |
| 6,548,298 B2 | 4/2003 | Villeponteau et al. |
| 6,551,774 B1 | 4/2003 | West et al. |
| 6,608,036 B1 | 8/2003 | Gryaznov et al. |
| 6,835,826 B2 | 12/2004 | Gryaznov et al. |
| 7,138,383 B2 | 11/2006 | Gryaznov et al. |
| 7,494,982 B2 | 2/2009 | Gryaznov et al. |
| 7,563,618 B2 | 7/2009 | Gryaznov et al. |
| 7,732,402 B2 | 6/2010 | Villeponteau et al. |
| 7,989,428 B2 | 8/2011 | Go et al. |
| 7,998,938 B2 | 8/2011 | Moore et al. |
| 8,153,604 B2 | 4/2012 | Deen et al. |
| 8,440,635 B2 | 5/2013 | Gryaznov et al. |
| 8,785,409 B2 | 7/2014 | Gryaznov et al. |
| 8,877,723 B2 | 11/2014 | Harley et al. |
| 9,072,790 B2 | 7/2015 | Gryaznov et al. |
| 2003/0175766 A1 | 9/2003 | West et al. |
| 2003/0190638 A1 | 10/2003 | West et al. |
| 2004/0234961 A1 | 11/2004 | Fordyce et al. |
| 2006/0128651 A1 | 6/2006 | Au et al. |
| 2006/0172960 A1 | 8/2006 | West et al. |
| 2006/0210980 A1 | 9/2006 | Cawthon |
| 2007/0166753 A1 | 7/2007 | Mass et al. |
| 2008/0220418 A1 | 9/2008 | Ballhause et al. |
| 2009/0035761 A1 | 2/2009 | Danenberg et al. |
| 2009/0142770 A1 | 6/2009 | Go et al. |
| 2009/0286853 A1 | 11/2009 | Gryaznov et al. |
| 2010/0104586 A1 | 4/2010 | Tressler et al. |

(Continued)

FOREIGN PATENT DOCUMENTS

EP 0 870 055 B1 10/1998
WO WO-93/23572 A1 11/1993

(Continued)

OTHER PUBLICATIONS

AACR Special Conference. (2010). "The Role of Telomeres and Telomerase in Cancer Research," AACR Special Conference, Feb. 27-Mar. 2, 2010, Fort Worth, Texas, Program for Saturday, Feb. 27, 2010, 8 pages.
Aviv, A. et al. (Nov. 1, 2011; e-pub. Aug. 8, 2011). "Impartial Comparative Analysis of Measurement of Leukocyte Telomere Length/DNA Content by Southern Blots and qPCR," Nuc. Acids Research 39(20):e134.
Baerlocher, G. M. et al. (2002). "Telomere Length Measurement by Fluorescence in Situ Hybridization and Flow Cytometry: Tips and Pitfalls," *Cytometry* 47:89-99.
Baerlocher, G. M. et al. (2006). "Flow Cytometry and FISH to Measure the Average Length of Telomeres (flow FISH)," *Nat. Protoc.* 1(5):2365-2376.
Baerlocher, G. M. et al. (2003). "Telomere Length Measurements in Leukocyte Subsets by Automated Multicolor Flow-FISH," *Cytometry A.* 55(1):1-6.
Baird, D.M. et al. (Feb. 2003; e-pub. Jan. 21, 2003). "Extensive Allelic Variation and Ultrashort Telomeres in Senescent Human Cells," *Nat. Genet.* 33(2):203-207.
Baerlocher, G.M. et al. (2009). "Leukemic T-PLL Cells Exhibit Short and Narrowly Distributed Telomere Lengths and High Telomerase Activities, Associated with Rapid and Dose-Dependent Cell Death Following Telomerase Inhibition by Imetelstat Sodium", *Blood*, 114: Abstract 2647.

(Continued)

*Primary Examiner* — Kimberly Chong
(74) *Attorney, Agent, or Firm* — Carol L. Francis; Glenn J. Foulds; Bozicevic, Field & Francis LLP

(57) ABSTRACT

Provided herein are methods for identifying individuals diagnosed with a cell proliferative disorder that will benefit from treatment with a telomerase inhibitor compound. Also provided herein are methods for treating these individuals with telomerase inhibitor compounds.

15 Claims, 9 Drawing Sheets

(56) References Cited

U.S. PATENT DOCUMENTS

| | | |
|---|---|---|
| 2010/0151477 A1 | 6/2010 | Cawthon |
| 2011/0263685 A1 | 10/2011 | Harley et al. |
| 2012/0129918 A1 | 5/2012 | Gryaznov et al. |
| 2012/0329858 A1 | 12/2012 | Gryaznov et al. |
| 2013/0065950 A1 | 3/2013 | Gryaznov et al. |
| 2013/0253042 A1 | 9/2013 | Gryaznov et al. |
| 2014/0248622 A1 | 9/2014 | Wang et al. |
| 2014/0329890 A1 | 11/2014 | Gryaznov et al. |
| 2014/0349292 A1 | 11/2014 | Gryaznov et al. |
| 2015/0152488 A1 | 6/2015 | Harley et al. |

FOREIGN PATENT DOCUMENTS

| | | |
|---|---|---|
| WO | WO-95/13382 A1 | 5/1995 |
| WO | WO-95/13383 A1 | 5/1995 |
| WO | WO-96/01835 A1 | 1/1996 |
| WO | WO-96/41016 A1 | 12/1996 |
| WO | WO-98/11207 A2 | 3/1998 |
| WO | WO-98/11207 A3 | 3/1998 |
| WO | WO-01/18015 A1 | 3/2001 |
| WO | WO-02/077184 A2 | 10/2002 |
| WO | WO-02/077184 A3 | 10/2002 |
| WO | WO-2004/029277 A2 | 4/2004 |
| WO | WO-2004/029277 A3 | 4/2004 |
| WO | WO-2005/023994 A2 | 9/2004 |
| WO | WO-2005/023994 A3 | 9/2004 |
| WO | WO-2006/113426 A2 | 10/2006 |
| WO | WO-2006/113426 A3 | 10/2006 |
| WO | WO-2006/113470 A2 | 10/2006 |
| WO | WO-2006/113470 A3 | 10/2006 |
| WO | WO-2008/054711 A2 | 10/2006 |
| WO | WO-2008/054711 A3 | 10/2006 |
| WO | WO-2006/124904 A2 | 11/2006 |
| WO | WO-2006/124904 A3 | 11/2006 |
| WO | WO-2007/067602 A1 | 6/2007 |
| WO | WO-2007/127163 A2 | 11/2007 |
| WO | WO-2007/127163 A3 | 11/2007 |
| WO | WO-2008/094640 A2 | 8/2008 |
| WO | WO-2008/094640 A3 | 8/2008 |
| WO | WO-2008/112129 A2 | 9/2008 |
| WO | WO-2008/112129 A3 | 9/2008 |
| WO | WO-2008/119027 A2 | 10/2008 |
| WO | WO-2008/119027 A3 | 10/2008 |
| WO | WO-2009/073751 A2 | 6/2009 |
| WO | WO-2009/073751 A3 | 6/2009 |
| WO | WO-2010/045245 A1 | 4/2010 |
| WO | WO-2012/135125 A1 | 10/2012 |

OTHER PUBLICATIONS

Bassett, E. et al. (2009). "Abstract #3482: Telomere shortening in human tumor cells in vitro and in vivo following treatment with telomerase inhibitor, GRN163L", *Cancer Res.*, 69:3482.

Bassett, K. (May 22, 2012). "Case Study: Identifying a Predictive Biomarker of Response to Imetelstate, a Telomerase Inhibitor" in Biomarker World Congress 2012, Pre-Conference Special Program, pp. 1-4, 6.

Brennan, S.K. et al. (Sep. 2010). "Telomerase Inhibition Targets Clonogenic Multiple Myeloma Cells Through Telomere Length-Dependent and Independent Mechanisms," *PloS One* 5(9):e12487, Eight Total Pages.

Canela, A. et al. (Mar. 27, 2007). "High-Throughput Telomere Length Quantification by FISH and its Application to Human Population Studies," *PNAS* 104(13):5300-5305.

Carpenter, R.L. et al. (1992). "Incidence and Risk Factors for Side Effects of Spinal Anesthesia," *Anesthesiology* 76(6):906-916.

Cawthon, R.M. (2009). "Telomere Length Measurement by a Novel Monochrome Multiplex Quantitative PCR Method," *Nuc. Acids Res.* 37(3):e21.

Cawthon, R.M. et al. (Feb. 1, 2003). "Association Between Telomere Length in Blood and Mortality in People Aged 60 Years or Older," *Lancet* 361(9355):393-395.

Cawthon, R.M. (2002). "Telomere Measurement by Quantitative PCR," *Nuc. Acids Res.* 30(10):e47.

Chen, Z. et al. (2003). "Consequences of Telomerase Inhibition and Combination Treatments for the Proliferation of Cancer Cells," *Cancer Research* 63:5917-5925.

clinicaltrials.gov (2015). "Imetelstat," located at <https://clinicaltrials.gov/ct2/results?term=imetelstat&Search=Search>, last visited on Mar. 25, 2015, Two Pages.

De Vivo, I. et al. (Apr. 2009; e-pub. Mar. 17, 2009). "A Prospective Study of Relative Telomere Length and Postmenopausal Breast Cancer Risk," *Cancer Epid. Biomarkers Prev.* 18(4):1152-1156.

Ehrlenbach, S. et al. (Dec. 2009; e-pub. Aug. 7, 2009). "Influences on the Reduction of Relative Telomere Length Over 10 Years in the Population-Based Bruneck Study: Introduction of a Well-Controlled High-Throughput Assay," *Int. J. Epidemiol.* 38(6):1725-1734.

Emrich, T. et al. (2000). "The LightCycler Instrument and MagNA Pure LC: An Automated System for the Evaluation of Telomerase Expression by Quantitative RT-PCR," *Biochemica* 4:10-22.

Engelhardt, M. et al. (1998). "Telomerase Activity and Telomere Length in Pediatric Patients with Malignancies Undergoing Chemotherapy," *Leukemia* 12(1):13-24.

Flores, I. et al. (Mar. 1, 2008; e-pub. Feb. 18, 2008). "The Longest Telomeres: A General Signature of Adult Stem Cell Compartments," *Genes Dev.* 22(5):654-667.

Frink, R.E. et al. (Oct. 27-29, 2011). "The Non-Small Cell Lung Cancers Exhibit Distinct Response Phenotypes to Telomerase Inhibitor Imetelstat," Presented at EORTC Meeting, Brussels, Belgium, (Abstract No. 7), located at <www.eortc.be/seminar/ENASCO2011/posters/pp007_Bassett.pdf>, last visited on Mar. 25, 2015, one page.

Frink, R.E. et al. (Apr. 15, 2010). "Abstract 3577: Sensitivity and Resistance of Non-Small Cell Lung Cancer to the Telomerase Inhibitor Imetelstat," *Cancer Research* 70:3577.

Frink, R.E. et al. (Apr. 15, 2011). "Abstract 4513: Predicting Response of Non-Small Cell Lung Cancer to the Telomerase Inhibitor Imetelstat," *Cancer Research* 71:4513.

Geron Corporation (Mar. 2010). "Press Release: Presentation's on Geron's Telomerase Inhibitor at AACR Special Conference," Three Total Pages.

Goldblatt, E.M. et al. (Jul. 2009). "The Telomerase Template Antagonist GRN163L Alters MDA-MB-231 Breast Cancer Cell Morphology, Inhibits Growth, and Augments the Effects of Paclitaxel," *Mol. Cancer Ther.* 8(7):2027-2035.

Harley, C.B. (Mar. 2008). "Telomerase and Cancer Therapeutics," *Nat. Rev. Cancer* 8(3):167-179.

Harley, C.B. et al. (May 31, 1990). "Telomeres Shorten During Ageing of Human Fibroblasts," *Nature* 345(6274):458-460.

Herbert, B-S. (2005). "Lipid Modification of GRN163, an N3'-->P5' thio-Phosphoramidate Oligonucleotide, Enhances the Potency of Telomerase Inhibition," *Oncogene* 24(33):5262-5268.

Hochreiter, A.E. et al. (May 15, 2006). "Telomerase Template Antagonist GRN163L Disrupts Telomere Maintenance, Tumor Growth, and Metastasis of Breast Cancer," *Clin. Cancer Res.* 12(10):3184-3192.

Joseph, I. et al. (Nov. 15, 2010). "The Telomerase Inhibitor Imetelstat Depletes Cancer Stem Cells in Breast and Pancreatic Cancer Cell Lines," *Cancer Research* 70(22):9494-9504.

Kim, N.W. et al. (Dec. 23, 1994). "Specific Association of Human Telomerase Activity with Immortal Cells and Cancer," *Science* 266(5193):2011-2015.

Kimura, M. et al. (Dec. 2007; e-pub. Sep. 26, 2007). "Leukocytes of Exceptionally Old Persons Display Ultra-Short Telomeres," *Am. J. Physiol. Regul. Integr. Comp. Physiol.* 293(6):R2210-R2217.

Koppelstaetter, C. et al. (2005). "Effect of Tissue Fixatives on Telomere Length Determination by Quantitative PCR," *Mech. Of Ageing and Dev.* 126(12):1331-1333.

Kozloff, M. et al. (2010). "Phase I Study of lmetelstat (GRN163L) in Combination with Paclitaxel (P) and Bevacizumab (B) in Patients (PTS) with Locally Recurrent or Metastatic Breast Cancer (MBC)," *ASCO*, One Page.

Ladetto, M. et al. (2004). "Telomere Length Correlates with Histopathogenesis According to the Germinal Center in Mature B-cell Lymphoproliferative Disorders," *Blood* 103(12):4644-4649.

(56) References Cited

OTHER PUBLICATIONS

Lee, J.-J. et al. (Aug. 2003; e-pub. Jun. 21, 2003). "Telomere Length Shortening in Non-Hodgkin's Lymphoma Patients Undergoing Chemotherapy," *Ann. Hematol.* 82(8):492-495.

Lehmann, U. et al. (2001). "Real-time PCR Analysis of DNA and RNA Extracted from Formalin-Fixed and Paraffin-Embedded Biopsies," *Methods* 25(4):409-418.

Marian, C.O. et al. (Jan. 1, 2010). "The Telomerase Antagonist, Imetelstat, Efficiently Targets Glioblastoma Tumor-Initiating Cells Leading to Decreased Proliferation and Tumor Growth," *Clin. Cancer Res.* 16(1):154-163.

Meeker, A.K. et al. (Apr. 2002). "Telomere Length Assessment in Human Archival Tissues: Combined Telomere Fluorescence in Situ Hybridization and Immunostaining", *American Journal of Pathology*, 160(4):1259-1268.

Meeker, A.K. et al. (May 15, 2004). "Telomere Length Abnormalities Occur Early in the Initiation of Epithelial Carcinogenesis," *Clin. Cancer Res.* 10(10):3317-3326.

Michalik, S.S. (Mar. 2008). "Overcoming Poor Quality DNA," located at <http://www.dddmag.com/articles/2008/03/overcoming-poor-guality-dna>, last visited on May 21, 2014, six pages.

Pooley, K.A. et al. (Apr. 15, 2010). "Telomere Length in Prospective and Retrospective Cancer Case-Control Studies," *Cancer Res.* 70(8):3170-3176.

Ratain, M.J. et al. (2008). "A Phase I Trial of GRN163L (GRN), a First-in-Class Telomerase Inhibitor, in Advanced Solid Tumors," *J. Clin. Oncology*, 2008 ASCO Annual Meeting Proceedings (Post Meeting Edition) 26(15S):3581 (Abstract only).

Ratain, M.J. et al. (Nov. 15-19, 2009). "Intermittent Dosing of Imetelstat Sodium, a Telomerase Inhibitor, Induces Drug Exposure Consistent with In Vivo Tumor Growth Inhibition," Presented at EORTC-NCI-AACR Symposium, Boston, MA., One Page.

Ratain, M.J. et al. (Nov. 16-19, 2010). "Imetelstat Sodium (GRN163L), a Telomerase Inhibitor: Tolerability, Pharmacokinetics and Pharmacodynamic Activity Using an Intermittent Once Every Four Weeks Dosing Schedule in Patients with Advanced Solid Tumors," Presented at EORTC-NCI-AACR Symposium, Berlin, Germany, One Page.

Shay, J.W. et al. (2006). "Telomerase Therapeutics for Cancer: Challenges and New Directions," *Nature Reviews Drug Discovery* 5(7):577-584.

Shay, J.W. et al. (2005). "Senescence and Immortalization: Role of Telomeres and Telomerase," *Carcinogenesis* 26(5):867-874.

Shayne, M. et al. (Oct. 1, 2007; e-pub. Aug. 17, 2007). "Dose Intensity and Hematologic Toxicity in Older Cancer Patients Receiving Systemic Chemotherapy," *Cancer* 110(7):1611-1620.

Shea-Herbert, B. et al. (2002). "Oligonucleotide N3'L P5' Phosphoramidates as Efficient Telomerase Inhibitors," *Oncogene* 21:638-642.

Shen, J. et al. (Jun. 1, 2007). "Short Telomere Length and Breast Cancer Risk: A Study in Sister Sets," *Cancer Res.* 67(11):5538-5544.

Shen, J. et al. (Apr. 1, 2009). "Telomere Length, Oxidative Damage, Antioxidants and Breast Cancer Risk," *Int. J. Cancer* 124(7):1637-1643.

Svenson, U. et al. (2008). "Breast Cancer Survival is Associated with Telomere Length in Peripheral Blood Cells," *Cancer Res.* 68(10):3618-3623.

Svenson, U. et al. (Apr. 1, 2009; e-pub. Mar. 24, 2009). "Telomere Length in Peripheral Blood Predicts Survival in Clear Cell Renal Cell Carcinoma," *Cancer Res.* 69(7):2896-2901.

Swarbrick, J. (2006). Dose Optimization in Drug Development, Taylor & Francis Group, LLC. New York, NY., 301 Total Pages.

Unryn, B.M. et al. (Nov. 1, 2006). " Acceleration of Telomere Loss by Chemotherapy is Greater in Older Patients with Locally Advanced Head and Neck Cancer," *Clin. Cancer Res.* 12(21):6345-6350.

Wang, H. et al. (Sep. 15, 2011). "Telomere Length Assessment in Human Archival Tumor Tissues by Quantitative PCR Method," Cancer Research 71(18), Supplement 2, Meeting Info: 2nd AACR International Conference on Frontiers in Basic Cancer Research, San Francisco, Sep. 14-18, 2011. Embase Abstract Accession No. 0051060743.

Wang, H. et al. (Mar. 31-Apr. 4, 2012). "Telomere Length Assessment in Human Archival Tumor Tissues by Quantitative PCR Method," AACR Meeting, One Page.

Xu, L. et al. (Oct. 26, 2007). "Human Cancer Cells Harbor T-Stumps, a Distinct Class of Extremely Short Telomeres," *Mol. Cell.* 28(2):315-327.

Yoon, S.Y. et al. (2007; e-pub. Apr. 11, 2007). "Telomere Length Shortening of Peripheral Blood Mononuclear Cells in Solid-Cancer Patients Undergoing Standard-Dose Chemotherapy Might be Correlated with Good Treatment Response and Neutropenia Severity," *Acta. Haematol.* 118(1):30-37.

Zheng, Y.-L. et al. (Apr. 2010). "Telomere Length from Blood Cells and Breast Cancer Risk: Investigations in Two Case-Control Studies," *Breast Cancer Res. Treat.* 120(3):769-775.

International Search Report dated Feb. 24, 2014, for PCT Patent Application No. PCT/US2013/072302, filed on Nov. 27, 2013, five pages.

U.S. Appl. No. 14/714,732, filed May 18, 2015, for Gryzanov et al. (copy not attached).

U.S. Appl. No. 14/720,466, filed May 22, 2015, for Gryzanov et al. (copy not attached).

U.S. Appl. No. 14/720,467, filed May 22, 2015, for Gryzanov et al. (copy not attached).

U.S. Appl. No. 14/728,572, filed Jun. 2, 2015, for Gryzanov et al. (copy not attached).

Zuo, L. et al. (Feb. 28, 2010). "Advances in Studies of Telomerase Inhibitors," *China Practical Medicine* 5(5), 8 pages. (Google Translation of Abstract).

Corey, David R., (2009) "Telomeres and Telomerase:From Discovery to Clinical Trials", Chemistry & Biology, 16:1219-1223.

Jackson, Shalmica R., et al., (2007) "Antiadhesive Effects of GRN163L—An Oligonucleotide N3'-P5'Thio-Phosphoramidate Targeting Telomerase", Cancer Res., 67(3)1121-1129.

Seimiya, Hiroyuki, 2005, "Telomere-directed molecular cancer therapeutics", Jounral of molecular targeted therapy for cancer, 3:24-30.

Remes, et al., 2000, "Telomere length and telomerase activity in malignant lymphomas at diagnosis and relapse", British Journal of Cancer, 82(3):601-607.

Ruden and Puri, 2013, "Novel anticancer therapeutics targeting telomerase", Cancer Treatment Reviews, 39:444-456.

Zuo, Lijuan, and Li, Hongxue, 2010, "Research Advances on Telomerase Inhibitors", China Prac Med, 5(5):4 pages.

SHORT TELOMERE
19 (33%)

DIAGNOSTIC MARKERS FOR TREATING CELL PROLIFERATIVE DISORDERS WITH TELOMERASE INHIBITORS

CROSS REFERENCE TO RELATED APPLICATIONS

This application is a continuation of U.S. patent application Ser. No. 13/802,035, filed on Mar. 13, 2013, now issued as U.S. Pat. No. 9,200,327, which claims the priority benefit of U.S. Provisional Patent Application No. 61/732,263, filed on Nov. 30, 2012. The contents of these applications are hereby incorporated by reference herein in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 707582000201SeqList.txt, date recorded: Feb. 26, 2016, size: 4 KB).

FIELD OF THE INVENTION

This invention relates to methods for identifying individuals having or suspected of having cancer who would benefit from treatment with telomerase inhibitor compounds as well as methods for treating these individuals.

BACKGROUND

Cancer is a leading cause of death worldwide. Despite significant advances in the field of chemotherapy, many of the most prevalent forms of cancer still resist chemotherapeutic intervention.

Telomeres are repetitive nucleic acid sequences present at the ends of the linear chromosomes of eukaryotic organisms. Telomere sequences, together with telomere-binding proteins, confer stability to chromosomes. Telomeres are generally composed of short tandem repeats with a repeat sequence unit specified by the telomerase enzyme particular to the organism. Telomere repeat sequences are known for a variety of organisms. The human telomere repeat sequence unit is $(TTAGGG)_n$. In addition to the double stranded repeat sequences, the 3' ends of some telomeres contain a single-stranded region, which for humans is located on the G rich strand.

Telomerase is a riboprotein which synthesizes telomeric DNA. In the absence of telomerase, telomeres gradually shorten because DNA polymerases are unable to replicate the ends of linear duplex DNA. The gradual shortening of the telomeres ultimately leads to cell cycle arrest or cell death. In humans, telomere length dependent mortality in cells occurs because of telomerase repression in normal somatic cells before birth, an initial telomere length at birth and throughout life, and tightly regulated expression of telomerase in progenitor or stem cells. Humans are born with "full-length" telomeres. As telomerase is down-regulated in somatic tissues, this leads to loss of telomeric DNA with cellular and chronological age. Thus telomeres act as a mitotic clock, conferring a finite capacity for division on normal human cells. Short telomeres impair the ability of stem cells to proliferate. For example, short telomeres in epidermal stems cells impair skin and hair growth.

Cancer cells generally undergo repeated rounds of cell division and have telomeres that are stable, but shorter than those in normal cells. Telomerase activation is necessary for most cancer cells to replicate indefinitely, and it enables tumor growth and metastasis (Kim et al., *Science* 266: 2011-2015; Shay J W and Wright W E., *Carcinogenesis* 26: 867-74 (2005)). Accordingly, inhibition of telomerase is considered a promising treatment strategy for a broad variety of solid tumor types and hematological malignancies (Harley C B, *Nature Rev. Cancer,* 8: 167-179 (2008)).

Unfortunately, many cancer patients do not obtain benefit from cytotoxic agents or targeted therapies such as telomerase inhibitors, but are still exposed to their toxic effects. For these reasons, novel methods for identifying cancer patients who will respond favorably to treatment with these therapeutics are urgently needed.

Throughout this specification, various patents, patent applications and other types of publications (e.g., journal articles) are referenced. The disclosure of all patents, patent applications, and publications cited herein are hereby incorporated by reference in their entirety for all purposes.

SUMMARY OF THE INVENTION

The invention provided herein discloses, inter alia, methods for identifying individuals who will benefit from treatment with telomerase inhibitor therapy and methods for treating the same.

Accordingly, in one aspect, provided herein are methods for selecting an individual diagnosed with or suspected of having cancer who will benefit from treatment with a telomerase inhibitor, the method comprising: determining relative telomere length by analyzing the relative length of telomeric nucleic acids in cancer cells present in a biological sample from the individual; and selecting an individual who will benefit from treatment with a telomerase inhibitor when the average relative telomere length in the cancer cells present in a biological sample from the individual is determined to be in the 50th percentile or less of a relative telomere length range determined from one or more known standards. In some embodiments of any of the embodiments disclosed herein, the telomerase inhibitor comprises an oligonucleotide. In some embodiments of any of the embodiments disclosed herein, the oligonucleotide is complementary to the RNA component of telomerase. In some embodiments of any of the embodiments disclosed herein, the oligonucleotide is 10-20 base pairs in length. In some embodiments of any of the embodiments disclosed herein, the oligonucleotide comprises the sequence TAGGGTTAGACAA (SEQ ID NO:3). In some embodiments of any of the embodiments disclosed herein, the oligonucleotide comprises at least one N3'→P5' thiophosphoramidate internucleoside linkage. In some embodiments of any of the embodiments disclosed herein, the oligonucleotide comprises N3'→P5' thiophosphoramidate internucleoside linkages. In some embodiments of any of the embodiments disclosed herein, the oligonucleotide comprises a lipid moiety linked to the 5' and/or 3' end of the oligonucleotide. In some embodiments of any of the embodiments disclosed herein, the lipid moiety is linked to the 5' and/or 3' end of the oligonucleotide via a linker. In some embodiments of any of the embodiments disclosed herein, the linker is a glycerol or aminoglycerol linker. In some embodiments of any of the embodiments disclosed herein, the lipid moiety is a palmitoyl (C16) moiety. In some embodiments of any of the embodiments disclosed herein, the telomerase inhibitor is Imetelstat. In some embodiments of any of the embodiments disclosed herein, the cancer is small cell lung cancer, breast cancer, prostate cancer, or a hematological cancer. In some embodiments of any of the embodiments disclosed herein, administration of the telomerase inhibitor results in decreased cancer cell proliferation and/or tumor growth. In some embodiments of any of the embodiments disclosed herein, administration of the telomerase inhibitor results in increased progression free survival in the individual. In some embodiments of any of the embodiments disclosed herein, the telomerase inhibitor is administered with a pharmaceutically acceptable excipient. In some embodiments of any of the embodiments disclosed herein, the telomerase inhibitor is formulated for oral, intravenous, subcutaneous, intramuscular, topical, intraperitoneal, intranasal, inhalation, intratumor, or intraocular administration. In some embodiments of any of the embodiments disclosed herein, administration of the therapeutically effective amount of the telomerase inhibitor comprises contacting one or more cancer cells with the telomerase inhibitor. In some embodiments of any of the embodiments disclosed herein, administration of the therapeutically effective amount of the telomerase inhibitor results in one or more of reduced cellular proliferation, increased apoptosis, or cellular senescence. In some embodiments of any of the embodiments disclosed herein, the method further comprises administering to the individual a therapeutically effective amount of one or more additional cancer therapeutic agents. In some embodiments of any of the embodiments disclosed herein, average telomere length is determined by qPCR, telo-FISH, or Southern Blot. In some embodiments of any of the embodiments disclosed herein, the individual is a human. In some embodiments of any of the embodiments disclosed herein, said one or more known standards are characterized cell lines. In some embodiments of any of the embodiments disclosed herein, the cell lines are selected from the group consisting of: M14Mel-cells, A549 cells, SK-Mel-5 cells, and Ovcar-5 cells. In some embodiments of any of the embodiments disclosed herein, the characterized cell lines are selected from cell lines representative of the type of biological sample of any of the embodiments disclosed herein. In some embodiments of any of the embodiments disclosed herein the characterized cell lines are non-small cell lung cancer cell lines, hepatocellular cell lines, or ovarian cell lines. In some embodiments of any of the embodiments disclosed herein, said one or more of the known standards is a telomere length range established from a plurality of naturally occurring tumors from a plurality of individuals. In some embodiments of any of the embodiments disclosed herein, said cancer cells from a plurality of naturally occurring tumors is of the same type as the cancer cells present in the biological sample from the individual. In some embodiments of any of the embodiments disclosed herein, the telomere length in the cancer cells present in the biological sample is determined to be in the 40th percentile, 35th percentile, 30th percentile, 25th percentile, 20th percentile, 15th percentile, 10th percentile, 5th percentile, or less than the telomere length range.

In another aspect, provided herein are methods for treating an individual diagnosed with or suspected of having cancer, the method comprising: determining relative telomere length by analyzing the relative length of telomeric nucleic acids in cancer cells present in a biological sample from the individual; selecting an individual who will benefit from treatment with a telomerase inhibitor when the average relative telomere length in the cancer cells present in a biological sample from the individual is determined to be in the 50th percentile or less of a relative telomere length range determined from one or more known standards; and administering a therapeutically effective amount of the telomerase inhibitor to the individual. In some embodiments of any of the embodiments disclosed herein, the telomerase inhibitor comprises an oligonucleotide. In some embodiments of any of the embodiments disclosed herein, the oligonucleotide is complementary to the RNA component of telomerase. In some embodiments of any of the embodiments disclosed herein, the oligonucleotide is 10-20 base pairs in length. In some embodiments of any of the embodiments disclosed herein, the oligonucleotide comprises the sequence TAGGGTTAGACAA (SEQ ID NO:3). In some embodiments of any of the embodiments disclosed herein, the oligonucleotide comprises at least one N3'→P5' thiophosphoramidate internucleoside linkage. In some embodiments of any of the embodiments disclosed herein, the oligonucleotide comprises N3'→P5' thiophosphoramidate internucleoside linkages. In some embodiments of any of the embodiments disclosed herein, the oligonucleotide comprises a lipid moiety linked to the 5' and/or 3' end of the oligonucleotide. In some embodiments of any of the embodiments disclosed herein, the lipid moiety is linked to the 5' and/or 3' end of the oligonucleotide via a linker. In some embodiments of any of the embodiments disclosed herein, the linker is a glycerol or aminoglycerol linker. In some embodiments of any of the embodiments disclosed herein, the lipid moiety is a palmitoyl (C16) moiety. In some embodiments of any of the embodiments disclosed herein, the telomerase inhibitor is Imetelstat. In some embodiments of any of the embodiments disclosed herein, the cancer is small cell lung cancer, breast cancer, prostate cancer, or a hematological cancer. In some embodiments of any of the embodiments disclosed herein, administration of the telomerase inhibitor results in decreased cancer cell proliferation and/or tumor growth. In some embodiments of any of the embodiments disclosed herein, administration of the telomerase inhibitor results in increased progression free survival in the individual. In some embodiments of any of the embodiments disclosed herein, the telomerase inhibitor is administered with a pharmaceutically acceptable excipient. In some embodiments of any of the embodiments disclosed herein, the telomerase inhibitor is formulated for oral, intravenous, subcutaneous, intramuscular, topical, intraperitoneal, intranasal, inhalation, intratumor, or intraocular administration. In some embodiments of any of the embodiments disclosed herein, administration of the therapeutically effective amount of the telomerase inhibitor comprises contacting one or more cancer cells with the telomerase inhibitor. In some embodiments of any of the embodiments disclosed herein, administration of the therapeutically effective amount of the telomerase inhibitor results in one or more of reduced cellular proliferation, increased apoptosis, or cellular senescence. In some embodiments of any of the embodiments disclosed herein, the method further comprises administering to the individual a therapeutically effective amount of one or more additional cancer therapeutic agents. In some embodiments of any of the embodiments disclosed herein, average telomere length is determined by qPCR, telo-FISH, or Southern Blot. In some embodiments of any of the embodiments disclosed herein, the individual is a human. In some embodiments of any of the embodiments disclosed herein, said one or more known standards are characterized cell lines. In some embodiments of any of the embodiments disclosed herein, the cell lines are selected from the group consisting of: M14Mel-cells, A549 cells, SK-Mel-5 cells, and Ovcar-5 cells. In some embodiments of any of the embodiments disclosed herein, the characterized cell lines are selected from cell lines representative of the type of biological sample of any of the embodiments disclosed herein. In some embodiments of any of the embodiments disclosed herein the characterized cell lines are non-small cell lung cancer cell lines, hepatocellular cell lines, or ovarian cell lines. In some embodiments of any of the embodiments disclosed herein, said one of more of the known standards is a telomere length range established from a plurality of naturally occurring tumors from a plurality of individuals. In some embodiments of any of the embodiments disclosed herein, said cancer cells from a plurality of naturally occurring tumors is of the same type as the cancer cells present in the biological sample from the individual. In some embodiments of any of the embodiments disclosed herein, the telomere length in the cancer cells present in the biological sample is determined to be in the 40th percentile, 35th percentile, 30th percentile, 25th percentile, 20th percentile, 15th percentile, 10th percentile, 5th percentile, or less than the telomere length range.

In yet other aspects, provided herein are methods for treating an individual diagnosed with or suspected of having cancer, the method comprising: administering a therapeutically effective amount of a telomerase inhibitor to the individual when the average relative telomere length in cancer cells present in a biological sample from the individual has been determined to be in the 50th percentile or less of a relative telomere length range determined from one or more known standards. In some embodiments of any of the embodiments disclosed herein, the telomerase inhibitor comprises an oligonucleotide. In some embodiments of any of the embodiments disclosed herein, the oligonucleotide is complementary to the RNA component of telomerase. In some embodiments of any of the embodiments disclosed herein, the oligonucleotide is 10-20 base pairs in length. In some embodiments of any of the embodiments disclosed herein, the oligonucleotide comprises the sequence TAGGGTTAGACAA (SEQ ID NO:3). In some embodiments of any of the embodiments disclosed herein, the oligonucleotide comprises at least one N3'→P5' thiophosphoramidate internucleoside linkage. In some embodiments of any of the embodiments disclosed herein, the oligonucleotide comprises N3'→P5' thiophosphoramidate internucleoside linkages. In some embodiments of any of the embodiments disclosed herein, the oligonucleotide comprises a lipid moiety linked to the 5' and/or 3' end of the oligonucleotide. In some embodiments of any of the embodiments disclosed herein, the lipid moiety is linked to the 5' and/or 3' end of the oligonucleotide via a linker. In some embodiments of any of the embodiments disclosed herein, the linker is a glycerol or aminoglycerol linker. In some embodiments of any of the embodiments disclosed herein, the lipid moiety is a palmitoyl (C16) moiety. In some embodiments of any of the embodiments disclosed herein, the telomerase inhibitor is Imetelstat. In some embodiments of any of the embodiments disclosed herein, the cancer is small cell lung cancer, breast cancer, prostate cancer, or a hematological cancer. In some embodiments of any of the embodiments disclosed herein, administration of the telomerase inhibitor results in decreased cancer cell proliferation and/or tumor growth. In some embodiments of any of the embodiments disclosed herein, administration of the telomerase inhibitor results in increased progression free survival in the individual. In some embodiments of any of the embodiments disclosed herein, the telomerase inhibitor is administered with a pharmaceutically acceptable excipient. In some embodiments of any of the embodiments disclosed herein, the telomerase inhibitor is formulated for oral, intravenous, subcutaneous, intramuscular, topical, intraperitoneal, intranasal, inhalation, intratumor, or intraocular administration. In some embodiments of any of the embodiments disclosed herein, administration of the therapeutically effective amount of the telomerase inhibitor comprises contacting one or more cancer cells with the telomerase inhibitor. In some embodiments of any of the embodiments disclosed herein, administration of the therapeutically effective amount of the telomerase inhibitor results in one or more of reduced cellular proliferation, increased apoptosis, or cellular senescence. In some embodiments of any of the embodiments disclosed herein, the method further comprises administering to the individual a therapeutically effective amount of one or more additional cancer therapeutic agents. In some embodiments of any of the embodiments disclosed herein, average telomere length is determined by qPCR, telo-FISH, or Southern Blot. In some embodiments of any of the embodiments disclosed herein, the individual is a human. In some embodiments of any of the embodiments disclosed herein, said one or more known standards are characterized cell lines. In some embodiments of any of the embodiments disclosed herein, the cell lines are selected from the group consisting of: M14Mel-cells, A549 cells, SK-Mel-5 cells, and Ovcar-5 cells. In some embodiments of any of the embodiments disclosed herein, the characterized cell lines are selected from cell lines representative of the type of biological sample of any of the embodiments disclosed herein. In some embodiments of any of the embodiments disclosed herein the characterized cell lines are non-small cell lung cancer cell lines, hepatocellular cell lines, or ovarian cell lines. In some embodiments of any of the embodiments disclosed herein, said one of more of the known standards is a telomere length range established from a plurality of naturally occurring tumors from a plurality of individuals. In some embodiments of any of the embodiments disclosed herein, said cancer cells from a plurality of naturally occurring tumors is of the same type as the cancer cells present in the biological sample from the individual. In some embodiments of any of the embodiments disclosed herein, the telomere length in the cancer cells present in the biological sample is determined to be in the 40th percentile, 35th percentile, 30th percentile, 25th percentile, 20th percentile, 15th percentile, 10th percentile, 5th percentile, or less than the telomere length range.

DETAILED DESCRIPTION OF THE INVENTION

Figure 1A:
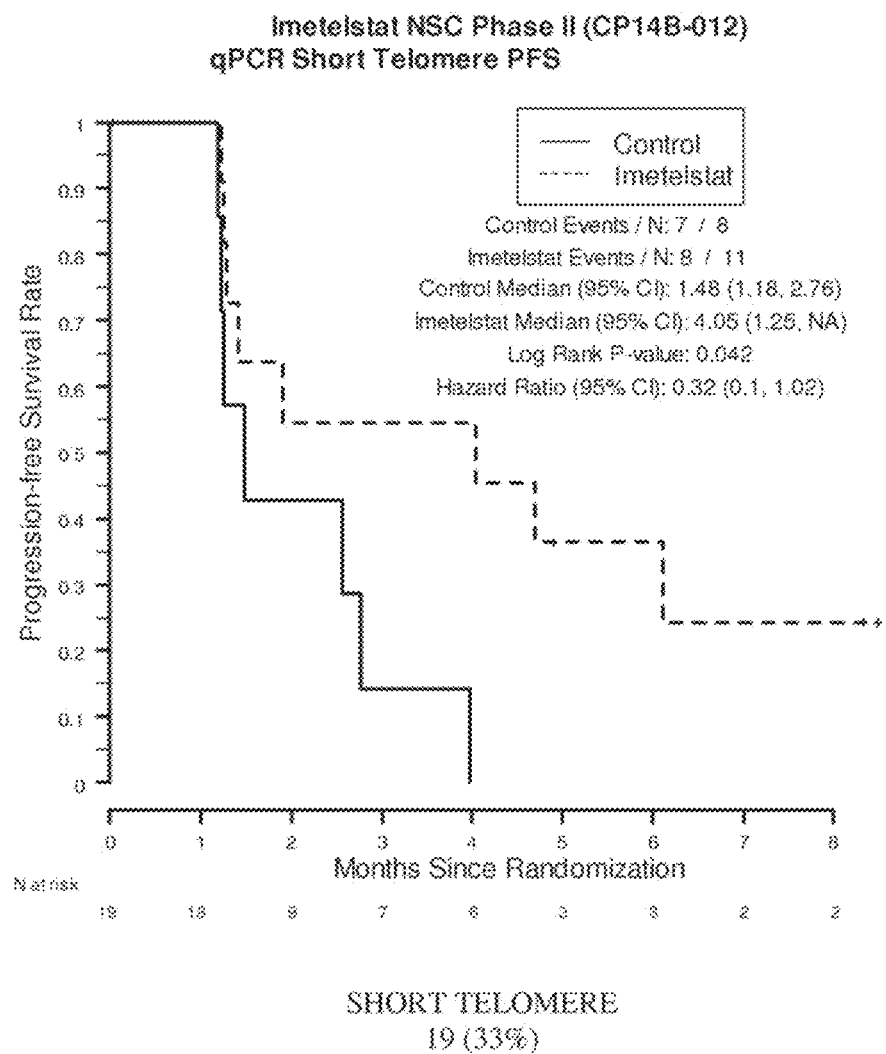
FIG. 1A depicts the progression-free survival (PFS) analysis of the short telomere subgroup (33 percentile) of the Imetelstat Non-Small Cell (NSC) Lung Cancer Phase II (CP14B-012) Study based on average telomere lengths determined using quantitative PCR (qPCR) as shown in Example 2.

This invention provides, inter alia, methods for identifying individuals suspected of having or that have been diagnosed with a cell proliferative disorder that will benefit from treatment with a telomerase inhibitor compound as well as methods for treating these individuals. Telomere length in cancer cells can vary from tumor to tumor. The inventors have observed that cancer cells with shorter telomere lengths are more responsive to treatment with telomerase inhibitor compounds (for example, Imetelstat) in comparison to cancer cells having longer telomere lengths. Accordingly, provided herein are methods for selecting an individual diagnosed with or suspected of having cancer that will benefit from treatment with a telomerase inhibitor. Also provided herein are methods for treating an individual diagnosed with or suspected of having cancer with a telomerase inhibitor, when the average relative telomere length in the cancer cells present in a biological sample from the individual is determined to be in the 50th percentile or less of a relative telomere length range determined from one or more known standards.

I. General Techniques

The practice of the invention will employ, unless otherwise indicated, conventional techniques in nucleic acid chemistry, molecular biology, microbiology, cell biology, biochemistry, and immunology, which are well known to those skilled in the art. Such techniques are explained fully in the literature, such as, *Molecular Cloning: A Laboratory Manual*, second edition (Sambrook et al., 1989) and *Molecular Cloning: A Laboratory Manual*, third edition (Sambrook and Russel, 2001), (jointly referred to herein as "Sambrook"); *Current Protocols in Molecular Biology* (F. M. Ausubel et al., eds., 1987, including supplements through 2001); *PCR: The Polymerase Chain Reaction*, (Mullis et al., eds., 1994). Nucleic acids can be synthesized in vitro by well-known chemical synthesis techniques, as described in, e.g., Carruthers (1982) Cold Spring Harbor *Symp. Quant. Biol.* 47:411-418; Adams (1983) *J. Am. Chem. Soc.* 105:661; Belousov (1997) *Nucleic Acids Res.* 5 25:3440-3444; Frenkel (1995) *Free Radic. Biol. Med.* 19:373-380; Blommers (1994) *Biochemistry* 33:7886-7896; Narang (1979) *Meth. Enzymol.* 68:90; Brown (1979) *Meth. Enzymol.* 68:109; Beaucage (1981) *Tetra. Lett.* 22:1859; Kornberg and Baker, *DNA Replication,* 2nd Ed. (Freeman, San Francisco, 1992); Scheit, *Nucleotide Analogs* (John Wiley, New York, 1980); Uhlmann and Peyman, *Chemical Reviews,* 90:543-584, 1990.

II. Definitions

The term "nucleoside" refers to a moiety having the general structure represented below, where B represents a nucleobase and the 2' carbon can be substituted as described below. When incorporated into an oligomer or polymer, the 3' carbon is further linked to an oxygen or nitrogen atom.

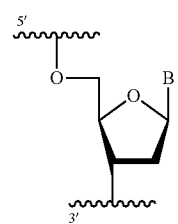

This structure includes 2'-deoxy and 2'-hydroxyl (i.e. deoxyribose and ribose) forms, and analogs. Less commonly, a 5'—NH group can be substituted for the 5'-oxygen. "Analogs", in reference to nucleosides, includes synthetic nucleosides having modified nucleobase moieties (see definition of "nucleobase" below) and/or modified sugar moieties, such as 2'-fluoro sugars, and further analogs. Such analogs are typically designed to affect binding properties, e.g., stability, specificity, or the like. The term nucleoside includes the natural nucleosides, including 2'-deoxy and 2'-hydroxyl forms, e.g., as described in Kornberg and Baker, *DNA Replication,* 2nd Ed. (Freeman, San Francisco, 1992), and analogs. "Analogs", in reference to nucleosides, includes synthetic nucleosides having modified nucleobase moieties (see definition of "nucleobase," infra) and/or modified sugar moieties, e.g., described generally by Scheit, *Nucleotide Analogs* (John Wiley, New York, 1980). Such analogs include synthetic nucleosides designed to enhance binding properties, e.g., stability, specificity, or the like, such as disclosed by Uhlmann and Peyman, Chemical Reviews 90:543-584, 1990). An oligonucleotide containing such nucleosides, and which typically contains synthetic nuclease-resistant internucleoside linkages, may itself be referred to as an "analog".

A "polynucleotide" or "oligonucleotide" refers to a ribose and/or deoxyribose nucleoside subunit polymer or oligomer having between about 2 and about 200 contiguous subunits. The nucleoside subunits can be joined by a variety of intersubunit linkages, including, but not limited to, phosphodiester, phosphotriester, methylphosphonate, P3'→N5' phosphoramidate, N3'→P5' phosphoramidate, N3→P5' thiophosphoramidate, and phosphorothioate linkages. The term also includes such polymers or oligomers having modifications, known to one skilled in the art, to the sugar (e.g., 2' substitutions), the base (see the definition of "nucleoside," supra), and the 3' and 5' termini. In embodiments where the oligonucleotide moiety includes a plurality of intersubunit linkages, each linkage may be formed using the same chemistry, or a mixture of linkage chemistries may be used. When an oligonucleotide is represented by a sequence of letters, such as "ATGUCCTG," it will be understood that the nucleotides are in 5'43' order from left to right. Representation of the base sequence of the oligonucleotide in this manner does not imply the use of any particular type of internucleoside subunit in the oligonucleotide.

A "nucleobase" includes (i) native DNA and RNA nucleobases (uracil, thymine, adenine, guanine, and cytosine), (ii) modified nucleobases or nucleobase analogs (e.g., 5-methylcytosine, 5-bromouracil, or inosine) and (iii) nucleobase analogs. A nucleobase analog is a compound whose molecular structure mimics that of a typical DNA or RNA base.

The term "lipid" is used broadly herein to encompass substances that are soluble in organic solvents, but sparingly soluble, if at all, in water. The term lipid includes, but is not limited to, hydrocarbons, oils, fats (such as fatty acids and glycerides), sterols, steroids and derivative forms of these compounds. In some embodiments, lipids are fatty acids and their derivatives, hydrocarbons and their derivatives, and sterols, such as cholesterol. Fatty acids usually contain even numbers of carbon atoms in a straight chain (commonly 12-24 carbons) and may be saturated or unsaturated, and can contain, or be modified to contain, a variety of substituent groups. For simplicity, the term "fatty acid" also encompasses fatty acid derivatives, such as fatty or esters. In some embodiments, the term "lipid" also includes amphipathic compounds containing both lipid and hydrophilic moieties.

As used herein "telomeric nucleic acids" means a nucleic acid sequence on a double or single stranded nucleic acid which encodes the telomere sequence of the mammal. In humans, the telomeric repeat sequence is TTAGGG on one strand and CCCTAA on the other strand.

A "telomerase inhibitor" is a compound which is capable of reducing or inhibiting the activity of telomerase reverse transcriptase enzyme in a mammalian cell. Such an inhibitor may be a small molecule compound, such as described herein, or an hTR template inhibitor including an oligonucleotide, such as described herein. In one aspect, the telomerase inhibitor is Imetelstat.

An "hTR template inhibitor" is a compound that blocks the template region (the region spanning nucleotides 30-67 of SEQ ID NO: 1 herein) of the RNA component of human telomerase, thereby inhibiting the activity of the enzyme. The inhibitor is typically an oligonucleotide that is able to hybridize to this region. In some embodiments, the oligonucleotide includes a sequence effective to hybridize to a more specific portion of this region, having sequence 5'-CUAACCCUAAC-3' (SEQ ID NO: 2), spanning nucleotides 46-56 of SEQ ID NO: 1 herein.

A compound is said to "inhibit the proliferation of cells" if the proliferation of cells in the presence of the compound is less than that observed in the absence of the compound. That is, proliferation of the cells is either slowed or halted in the presence of the compound. Inhibition of cancer-cell proliferation may be evidenced, for example, by reduction in the number of cells or rate of expansion of cells, reduction in tumor mass or the rate of tumor growth, or increase in survival rate of a subject being treated.

An oligonucleotide having "nuclease-resistant linkages" refers to one whose backbone has subunit linkages that are substantially resistant to nuclease cleavage, in non-hybridized or hybridized form, by common extracellular and intracellular nucleases in the body; that is, the oligonucleotide shows little or no nuclease cleavage under normal nuclease conditions in the body to which the oligonucleotide is exposed. The N3'→P5' phosphoramidate (NP) or N3'→P5' thiophosphoramidate (NPS) linkages described below are nuclease resistant.

An "individual" can be a mammal, such as any common laboratory model organism. Mammals include, but are not limited to, humans and non-human primates, farm animals, sport animals, pets, mice, rats, and other rodents. In some embodiments, an individual is a human.

As used herein, "treatment" (and grammatical variations thereof such as "treat" or "treating") refers to clinical intervention designed to alter the natural course of the individual or cell being treated during the course of clinical pathology. Desirable effects of treatment include, but are not limited to, decreasing the rate of disease progression, amelioration or palliation of the disease state, and remission or improved prognosis.

As used herein, "prevention" includes providing prophylaxis with respect to occurrence or recurrence of a disease or the symptoms associated with a disease in an individual. An individual may be predisposed to, susceptible to, or at risk of developing a disease, but has not yet been diagnosed with the disease.

An "effective amount" or "therapeutically effective amount" refers to an amount of therapeutic compound, such as telomerase inhibitor, administered to a mammalian subject, either as a single dose or as part of a series of doses, which is effective to produce a desired therapeutic effect.

A "biological sample" is a sample of tissue, blood, lymphatic fluid, or cerebral fluid obtained from the individual. The biological sample may be a sample obtained during the removal of a cancerous growth from the individual. The biological sample could include fresh tissue or formalin fixed paraffin embedded tissue or frozen tissue.

As used herein, the singular form "a", "an", and "the" includes plural references unless indicated otherwise.

It is understood that aspects and embodiments of the invention described herein include "comprising," "consisting," and "consisting essentially of" aspects and embodiments.

It is intended that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

III. Telomerase Inhibitor Compounds

Telomerase is a ribonucleoprotein that catalyzes the addition of telomeric repeat sequences (having the sequence 5'-TTAGGG-3' in humans) to chromosome ends. See e.g. Blackburn, 1992, *Ann. Rev. Biochem.* 61:113-129. The enzyme is expressed in most cancer cells but not in mature somatic cells. Loss of telomeric DNA may play a role in triggering cellular senescence; see Harley, 1991, *Mutation Research* 256:271-282. A variety of cancer cells have been shown to be telomerase-positive, including cells from cancer of the skin, connective tissue, adipose, breast, lung, stomach, pancreas, ovary, cervix, uterus, kidney, bladder, colon, prostate, central nervous system (CNS), retina and hematologic tumors (such as myeloma, leukemia and lymphoma). Targeting of telomerase can be effective in providing treatments that discriminate between malignant and normal cells to a high degree, avoiding many of the deleterious side effects that can accompany chemotherapeutic regimens which target dividing cells indiscriminately.

Inhibitors of telomerase identified to date include oligonucleotides (for example, oligonucleotides having nuclease resistant linkages) as well as small molecule compounds. Further information regarding telomerase inhibitor compounds can be found in U.S. Pat. No. 7,998,938, the disclosure of which is incorporated by reference herein in its entirety.

A. Small Molecule Compounds

Small molecule inhibitors of telomerase include, for example, BRACO19 ((9-(4-(N,N-dimethylamino)phenylamino)-3,6-bis(3-pyrrolodino propionamido)acridine (see *Mol. Pharmacol.* 61(5):1154-62, 2002); DODC (diethyloxadicarbocyanine), and telomestatin. These compounds may act as G-quad stabilizers, which promote the formation of an inactive G-quad configuration in the RNA component of telomerase. Other small molecule inhibitors of telomerase include BIBR1532 (2-[(E)-3-naphthen-2-yl but-2-enoylamino]benzoic acid) (see Ward & Autexier, *Mol. Pharmacol.* 68:779-786, 2005; also *J. Biol. Chem.* 277(18):15566-72, 2002); AZT and other nucleoside analogs, such as ddG and ara-G (see, for example, U.S. Pat. Nos. 5,695,932 and 6,368,789), and certain thiopyridine, benzo[b]thiophene, and pyrido[b]thiophene derivatives, described by Gaeta et al. in U.S. Pat. Nos. 5,767,278, 5,770,613, 5,863,936, 5,656, 638 and 5,760,062, the disclosures of which are incorporated by reference herein. Another example is 3-chlorobenzo [b]thiophene-2-carboxy-2'-[(2,5-dichlorophenyl amino) thia]hydrazine, described in U.S. Pat. No. 5,760,062 and which is incorporated by reference herein.

B. Oligonucleotide-Based Telomerase Inhibitors: Sequence and Composition

The genes encoding both the protein and RNA components of human telomerase have been cloned and sequenced (see U.S. Pat. Nos. 6,261,836 and 5,583,016, respectively, both of which are incorporated herein by reference). Oligonucleotides can be targeted against the mRNA encoding the telomerase protein component (the human form of which is known as human telomerase reverse transcriptase, or hTERT) or the RNA component of the telomerase holoenzyme (the human form of which is known as human telomerase RNA, or hTR).

The nucleotide sequence of the RNA component of human telomerase (hTR) is shown in the Sequence Listing below (SEQ ID NO: 1), in the 5'43' direction. The sequence is shown using the standard abbreviations for ribonucleotides; those of skill in the art will recognize that the sequence also represents the sequence of the cDNA, in which the ribonucleotides are replaced by deoxyribonucleotides, with uridine (U) being replaced by thymidine (T). The template sequence of the RNA component is located within the region defined by nucleotides 46-56 (5'-CUAAC-CCUAAC-3') (SEQ ID NO:2), which is complementary to a telomeric sequence composed of about one-and-two-thirds telomeric repeat units. The template region functions to specify the sequence of the telomeric repeats that telomerase adds to the chromosome ends and is essential to the activity of the telomerase enzyme (see e.g. Chen et al., *Cell* 100: 503-514, 2000; Kim et al., *Proc. Natl. Acad. Sci. USA* 98 (14):7982-7987, 2001). The design of antisense, ribozyme or small interfering RNA (siRNA) agents to inhibit or cause the destruction of mRNAs is well known (see, for example, Lebedeva, I, et al. *Annual Review of Pharmacology and Toxicology*, Vol. 41: 403-419, April 2001; Macejak, D, et al., *Journal of Virology*, Vol. 73 (9): 7745-7751, September 1999, and Zeng, Y. et al., *PNAS* Vol. 100 (17) p. 9779-9784, Aug. 19, 2003) and such agents may be designed to target the hTERT mRNA and thereby inhibit production of hTERT protein in a target cell, such as a cancer cell (see, for example, U.S. Pat. Nos. 6,444,650 and 6,331,399).

Oligonucleotides targeting hTR (that is, the RNA component of the enzyme) act as inhibitors of telomerase enzyme activity by blocking or otherwise interfering with the interaction of hTR with the hTERT protein, which interaction is necessary for telomerase function (see, for example, Villeponteau et al., U.S. Pat. No. 6,548,298).

A preferred target region of hTR is the template region, spanning nucleotides 30-67 of SEQ ID NO:1 (GGGUUGCGGAGGGUGGGCCUGGGAGGGGUG-GUGGCCAUUU UUUGUCUAACCCUAACUGA-GAAGGGCGUAGGCGCCGUGCUUUUGCUCCCC GCGCGCUGUUUUUCUCGCUGACUUUCA-GCGGGCGGAAAAGCCUCGGCCUG CCGCCUUC-CACCGUUCAUUCUAGAGCAAACAAAAAAUGUCA-GCUGCUGGC CCGUUCGCCUCCCGGGGACCUGCGGCGGGUCGC-CUGCCCAGCCCCCGAAC CCCGCCUGGAGCCGCG-GUCGGCCCGGGGCUUCUCCGGAGGCACCCACUGC CACCGCGAAGAGUUGGGCUCUGUCAGCCGCGG-GUCUCUCGGGGGCGAGGG CGAGGUUCAC-CGUUUCAGGCCGCAGGAAGAGGAACGGAGCGA-GUCCCGCC GCGGCGCGAUUCCCUGAGCUGUGGGACGUGCAC-CCAGGACUCGGCUCACA CAUGCAGUUCGCUUUC-CUGUUGGUGGGGGGAACGCCGAUCGUGCG-CAUCC GUCACCCCUCGCCGGCAGUGGGGGCUUGUGAAC-CCCCAAACCUGACUGAC UGGGCCAGUGUGCU). Oligonucleotides targeting this region are referred to herein as "hTR template inhibitors" (see e.g. Herbert et al., *Oncogene* 21 (4):638-42 (2002).) Preferably, such an oligonucleotide includes a sequence which is complementary or near-complementary to some portion of the 11-nucleotide region having sequence 5'-CUAACCCUAAC-3' (SEQ ID NO:2), spanning nucleotides 46-56 of SEQ ID NO: 1.

Another preferred target region is the region spanning nucleotides 137-179 of hTR (see Pruzan et al., *Nucl. Acids Research*, 30:559-568, 2002). Within this region, the sequence spanning 141-153 is a preferred target. PCT publication WO 98/28442 describes the use of oligonucleotides of at least 7 nucleotides in length to inhibit telomerase, where the oligonucleotides are designed to be complementary to accessible portions of the hTR sequence outside of the template region, including nucleotides 137-196, 290-319, and 350-380 of hTR.

The region of the therapeutic oligonucleotide that is targeted to the hTR sequence is preferably exactly complementary to the corresponding hTR sequence. While mismatches may be tolerated in certain instances, they are expected to decrease the specificity and activity of the resultant oligonucleotide conjugate. In particular embodiments, the base sequence of the oligonucleotide is thus selected to include a sequence of at least 5 nucleotides exactly complementary to the hTR target, and enhanced telomerase inhibition may be obtained if increasing lengths of complementary sequence are employed, such as at least 8, at least 10, at least 12, at least 13 or at least 15 nucleotides exactly complementary to the hTR target. In other embodiments, the sequence of the oligonucleotide includes a sequence of from at least 5 to 20, from at least 8 to 20, from at least 10 to 20 or from at least 10 to 15 nucleotides exactly complementary to the hTR target sequence.

Optimal telomerase inhibitory activity may be obtained when the full length of the oligonucleotide is selected to be complementary to the hTR target sequence. However, it is not necessary that the full length of the oligonucleotide is exactly complementary to the target sequence, and the oligonucleotide sequence may include regions that are not complementary to the target sequence. Such regions may be added, for example, to confer other properties on the compound, such as sequences that facilitate purification. Alternatively, an oligonucleotide may include multiple repeats of a sequence complementary to an hTR target sequence.

If the oligonucleotide is to include regions that are not complementary to the target sequence, such regions are typically positioned at one or both of the 5' or 3' termini. Exemplary sequences targeting human telomerase RNA (hTR) include the following:

The internucleoside linkages in the oligonucleotide may include any of the available oligonucleotide chemistries, e.g. phosphodiester, phosphotriester, methylphosphonate, P3'→N5' phosphoramidate, N3'→P5' phosphoramidate, N3'→P5' thiophosphoramidate, and phosphorothioate. Typically, but not necessarily, all of the internucleoside linkages within the oligonucleotide will be of the same type, although the oligonucleotide component may be synthesized using a mixture of different linkages.

In some embodiments, the oligonucleotide has at least one N3'→P5' phosphoramidate (NP) or N3'→P5' thiophosphoramidate (NPS) linkage, which linkage may be represented by the structure: 3'-(—NH—P(=O)(—XR)—O—)-5', wherein X is O or S and R is selected from the group consisting of hydrogen, alkyl, and aryl; and pharmaceutically acceptable salts thereof, when XR is OH or SH. In other embodiments, the oligonucleotide includes all NP or, in some embodiments, all NPS linkages.

In one embodiment, the sequence for an hTR template inhibitor oligonucleotide is the sequence complementary to nucleotides 42-54 of SEQ ID NO: 1 supra. The oligonucleotide having this sequence (TAGGGTTAGACAA; SEQ ID NO:3) and N3'→P5' thiophosphoramidate (NPS) linkages is designated herein as GRN163. See, for example, Asai et al., *Cancer Research* 63:3931-3939 (2003) and Gryaznov et al., *Nucleosides Nucleotides Nucleic Acids* 22(5-8):577-81 (2003).

The oligonucleotide GRN163 administered alone has shown inhibitory activity in vitro in cell culture, including epidermoid carcinoma, breast epithelium, renal carcinoma, renal adenocarcinoma, pancreatic, brain, colon, prostate, leukemia, lymphoma, myeloma, epidermal, cervical, ovarian and liver cancer cells.

The oligonucleotide GRN163 has also been tested and shown to be therapeutically effective in a variety of animal tumor models, including ovarian and lung, both small cell and non-small cell (see, e.g., U.S. Pat. No. 7,998,938, the disclosure of which is incorporated by reference).

C. Lipid-Oligonucleotide Conjugates

In some aspects, the oligonucleotide-based telomerase inhibitors disclosed herein includes at least one covalently linked lipid group (see U.S. Pub. No. 2005/0113325, which is incorporated herein by reference). This modification provides superior cellular uptake properties, such that an equivalent biological effect may be obtained using smaller amounts of the conjugated oligonucleotide compared to the unmodified form. When applied to the human therapeutic setting, this may translate to reduced toxicity risks, and cost savings.

The lipid group L is typically an aliphatic hydrocarbon or fatty acid, including derivatives of hydrocarbons and fatty acids, with examples being saturated straight chain compounds having 14-20 carbons, such as myristic (tetradecanoic) acid, palmitic (hexadecanoic) acid, and stearic (octadeacanoic) acid, and their corresponding aliphatic hydrocarbon forms, tetradecane, hexadecane and octadecane. Examples of other suitable lipid groups that may be employed are sterols, such as cholesterol, and substituted fatty acids and hydrocarbons, particularly polyfluorinated forms of these groups. The scope of the lipid group L includes derivatives such as amine, amide, ester and carbamate derivatives. The type of derivative is often determined by the mode of linkage to the oligonucleotide, as exemplified below.

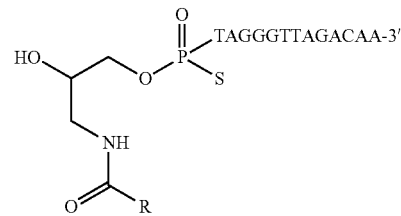

In one exemplary structure, the lipid moiety is palmitoyl amide (derived from palmitic acid), conjugated through an aminoglycerol linker to the 5' thiophosphate group of an NPS-linked oligonucleotide. The NPS oligonucleotide having the sequence shown for GRN163 and conjugated in this manner (as shown below) is designated GRN163L (Imetelstat) herein. In a second exemplary structure, the lipid, as a palmitoyl amide, is conjugated through the terminal 3' amino group of an NPS oligonucleotide.

D. Pharmaceutical compositions

In some aspects of the present invention, when employed as pharmaceuticals, the telomerase inhibitor compounds disclosed herein can be formulated with a pharmaceutically acceptable excipient or carrier to be formulated into a pharmaceutical composition.

When employed as pharmaceuticals, the telomerase inhibitor compounds can be administered in the form of pharmaceutical compositions. These compounds can be administered by a variety of routes including oral, rectal, transdermal, subcutaneous, intravenous, intramuscular, and intranasal. These compounds are effective as both injectable and oral compositions. Such compositions are prepared in a manner well known in the pharmaceutical art and comprise at least one active compound. When employed as oral compositions, the telomerase inhibitor compounds disclosed herein are protected from acid digestion in the stomach by a pharmaceutically acceptable protectant.

This invention also includes pharmaceutical compositions which contain, as the active ingredient, a telomerase inhibitor compound associated with one or more pharmaceutically acceptable excipients or carriers. In making the compositions of this invention, the active ingredient is usually mixed with an excipient or carrier, diluted by an excipient or carrier or enclosed within such an excipient or carrier which can be in the form of a capsule, sachet, paper or other container. When the excipient or carrier serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, it may be necessary to mill the active lyophilized compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable excipients or carriers include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions can be formulated in a unit dosage form, each dosage containing from about 5 mg to about 100 mg or more, such as any of about 1 mg to about 5 mg, 1 mg to about 10 mg, about 1 mg to about 20 mg, about 1 mg to about 30 mg, about 1 mg to about 40 mg, about 1 mg to about 50 mg, about 1 mg to about 60 mg, about 1 mg to about 70 mg, about 1 mg to about 80 mg, or about 1 mg to about 90 mg, inclusive, including any range in between these values, of the active ingredient. The term "unit dosage forms" refers to physically discrete units suitable as unitary dosages for individuals, each unit containing a predetermined quantity of active material calculated to produce the desired therapeutic effect, in association with a suitable pharmaceutical excipient or carrier.

The telomerase inhibitor compounds are effective over a wide dosage range and are generally administered in a therapeutically effective amount. It will be understood, however, that the amount of the telomerase inhibitor compounds actually administered will be determined by a physician, in the light of the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient telomerase inhibitor compound is mixed with a pharmaceutical excipient or carrier to form a solid preformulation composition containing a homogeneous mixture of a compound of the present invention. When referring to these preformulation compositions as homogeneous, it is meant that the active ingredient is dispersed evenly throughout the composition so that the composition can be readily subdivided into equally effective unit dosage forms such as tablets, pills and capsules.

The tablets or pills of the present invention can be coated or otherwise compounded to provide a dosage form affording the advantage of prolonged action and to protect the telomerase inhibitor compounds from acid hydrolysis in the stomach. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the novel compositions of the present invention can be incorporated for administration orally or by injection include aqueous solutions, suitably flavored syrups, aqueous or oil suspensions, and flavored emulsions with edible oils such as corn oil, cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions can contain suitable pharmaceutically acceptable excipients as described supra. The compositions can be administered by the oral or nasal respiratory route for local or systemic effect. Compositions in pharmaceutically acceptable solvents can be nebulized by use of inert gases. Nebulized solutions can be inhaled directly from the nebulizing device or the nebulizing device can be attached to a face mask tent, or intermittent positive pressure breathing machine. Solution, suspension, or powder compositions can also be administered, orally or nasally, from devices which deliver the formulation in an appropriate manner.

IV. Methods of the Invention

In some aspects, methods for selecting an individual diagnosed with or suspected of having cancer who will benefit from treatment with a telomerase inhibitor are provided herein. These methods are based on determining the average relative length of telomeres in cancer cells present in a biological sample from the individual. If the average telomere length in cancer cells present in a biological sample from the individual is determined to be in the 50th percentile or less of a relative telomere length range determined from one or more known standards, then the individual diagnosed with or suspected of having cancer will benefit from treatment with a telomerase inhibitor (such as any of the telomerase inhibitors provided herein). In other aspects, the telomerase inhibitor compounds disclosed herein can be used for the treatment and/or prevention of a cell proliferative disorder (such as cancer) when the average relative telomere length in cancer cells present in a biological sample from the individual is determined to be in the 50th percentile or less of a relative telomere length range determined from one or more known standards.

A. Cell Proliferative Disorders

A "proliferative disorder" is any cellular disorder in which the cells proliferate more rapidly than normal tissue growth. Thus a "proliferating cell" is a cell that is proliferating more rapidly than normal cells. The proliferative disorder includes, but is not limited to, neoplasms. A "neoplasm" is an abnormal tissue growth, generally forming a distinct mass that grows by cellular proliferation more rapidly than normal tissue growth. Neoplasms show partial or total lack of structural organization and functional coordination with normal tissue. These can be broadly classified into three major types. Malignant neoplasms arising from epithelial structures are called carcinomas, malignant neoplasms that originate from connective tissues such as muscle, cartilage, fat or bone are called sarcomas and malignant tumors affecting hematopoetic structures (structures pertaining to the formation of blood cells) including components of the immune system, are called leukemias and lymphomas. A tumor is the neoplastic growth of the disease cancer. As used herein, a neoplasm, also referred to as a "tumor", is intended to encompass hematopoietic neoplasms as well as solid neoplasms. Other proliferative disorders include, but are not limited to, neurofibromatosis.

The telomerase inhibitor compounds (such as in compositions) provided herein are useful for modulating disease states associated with dysregulation of telomere length. In some embodiments, the cell proliferative disorder is associated with increased expression or activity of telomerase or cellular growth, or both. In some embodiments, the cell proliferation is cancer.

The methods described herein are also useful for treating solid tumors (such as advanced solid tumors). In some embodiments, there is provided a method of treating lung cancer, including, for example, non-small cell lung cancer (NSCLC, such as advanced NSCLC), small cell lung cancer (SCLC, such as advanced SCLC), and advanced solid tumor malignancy in the lung. In some embodiments, there is provided a method of treating any of ovarian cancer, head and neck cancer, gastric malignancies such as gastric cancer, gastrointestinal cancer such as upper gastrointestinal cancer, gallbladder cancer, bladder cancer, glioblastoma, sarcomas such as osteosarcoma, Ewing sarcoma and meningiosarcoma, melanoma (including metastatic melanoma and malignant melanoma), colorectal cancer, and pancreatic cancer.

In some embodiments, the method is useful for treating one or more of the following: cutaneous T cell lymphoma (CTCL), leukemia, follicular lymphoma, Hodgkin lymphoma, and acute myeloid leukemia.

In some embodiments, the disease is a cancer of any one of the following: basal cell carcinoma, medulloblastoma, glioblastoma, multiple myeloma, chronic myelogenous leukemia (CML), acute myelogenous leukemia, pancreatic cancer, lung cancer (small cell lung cancer and non-small cell lung cancer), esophageal cancer, stomach cancer, billary cancer, prostate cancer, liver cancer, hepatocellular cancer, gastrointestinal cancer, gastric cancer, gallbladder cancer, ovarian cancer and bladder cancer. In some embodiments, the cancer is selected from the group consisting of pancreas ductal adenocarcinoma, colon adenocarcinoma, and ovary cystadenocarcinoma. In some embodiments, the cancer is pancreas ductal adenocarcinoma. In some embodiments, the cancer is a tumor that is poorly perfused and/or poorly vascularized.

In some embodiments, the cancer is pancreatic cancer, including for example pancreatic adenocarcinoma, pancreatic adenosquamous carcinoma, pancreatic squamous cell carcinoma, and pancreatic giant cell carcinoma. In some embodiments, the pancreatic cancer is exocrine pancreatic cancer. In some embodiments, the pancreatic cancer is endocrine pancreatic cancer (such as islet cell carcinoma). In some embodiments, the pancreatic cancer is advanced metastatic pancreatic cancer.

Other examples of cancers that can be treated by the methods of the invention include, but are not limited to, adenocortical carcinoma, agnogenic myeloid metaplasia, AIDS-related cancers (e.g., AIDS-related lymphoma), anal cancer, appendix cancer, astrocytoma (e.g., cerebellar and cerebral), basal cell carcinoma, bile duct cancer (e.g., extrahepatic), bladder cancer, bone cancer, (osteosarcoma and malignant fibrous histiocytoma), brain tumor (e.g., glioma, brain stem glioma, cerebellar or cerebral astrocytoma (e.g., pilocytic astrocytoma, diffuse astrocytoma, anaplastic (malignant) astrocytoma), malignant glioma, ependymoma, oligodenglioma, meningioma, meningiosarcoma, craniopharyngioma, haemangioblastomas, medulloblastoma, supratentorial primitive neuroectodermal tumors, visual pathway and hypothalamic glioma, and glioblastoma), breast cancer, bronchial adenomas/carcinoids, carcinoid tumor (e.g., gastrointestinal carcinoid tumor), carcinoma of unknown primary, central nervous system lymphoma, cervical cancer, colon cancer, colorectal cancer, chronic myeloproliferative disorders, endometrial cancer (e.g., uterine cancer), ependymoma, esophageal cancer, Ewing's family of tumors, eye cancer (e.g., intraocular melanoma and retinoblastoma), gallbladder cancer, gastric (stomach) cancer, gastrointestinal carcinoid tumor, gastrointestinal stromal tumor (GIST), germ cell tumor, (e.g., extracranial, extragonadal, ovarian), gestational trophoblastic tumor, head and neck cancer, hepatocellular (liver) cancer (e.g., hepatic carcinoma and heptoma), hypopharyngeal cancer, islet cell carcinoma (endocrine pancreas), laryngeal cancer, laryngeal cancer, leukemia, lip and oral cavity cancer, oral cancer, liver cancer, lung cancer (e.g., small cell lung cancer, non-small cell lung cancer, adenocarcinoma of the lung, and squamous carcinoma of the lung), lymphoid neoplasm (e.g., lymphoma), medulloblastoma, ovarian cancer, mesothelioma, metastatic squamous neck cancer, mouth cancer, multiple endocrine neoplasia syndrome, myelodysplastic syndromes, myelodysplastic/myeloproliferative diseases, nasal cavity and paranasal sinus cancer, nasopharyngeal cancer, neuroblastoma, neuroendocrine cancer, oropharyngeal cancer, ovarian cancer (e.g., ovarian epithelial cancer, ovarian germ cell tumor, ovarian low malignant potential tumor), pancreatic cancer, parathyroid cancer, penile cancer, cancer of the peritoneal, pharyngeal cancer, pheochromocytoma, pineoblastoma and supratentorial primitive neuroectodermal tumors, pituitary tumor, pleuropulmonary blastoma, lymphoma, primary central nervous system lymphoma (microglioma), pulmonary lymphangiomyomatosis, rectal cancer, renal cancer, renal pelvis and ureter cancer (transitional cell cancer), rhabdomyosarcoma, salivary gland cancer, skin cancer (e.g., non-melanoma (e.g., squamous cell carcinoma), melanoma, and Merkel cell carcinoma), small intestine cancer, squamous cell cancer, testicular cancer, throat cancer, thymoma and thymic carcinoma, thyroid cancer, tuberous sclerosis, urethral cancer, vaginal cancer, vulvar cancer, Wilms' tumor, and post-transplant lymphoproliferative disorder (PTLD), abnormal vascular proliferation associated with phakomatoses, edema (such as that associated with brain tumors), and Meigs' syndrome.

In some embodiments, the cancer is a solid tumor (such as advanced solid tumor). Solid tumor includes, but is not limited to, sarcomas and carcinomas such as fibrosarcoma, myxosarcoma, liposarcoma, chondrosarcoma, osteogenic sarcoma, osteosarcoma, chordoma, angiosarcoma, endotheliosarcoma, lymphangiosarcoma, lymphangioendotheliosarcoma, Kaposi's sarcoma, soft tissue sarcoma, uterine sacronomasynovioma, mesothelioma, Ewing's tumor, leiomyosarcoma, rhabdomyosarcoma, meningiosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma (including for example adenocarcinoma, clear cell renal cell carcinoma, papillary renal cell carcinoma, chromophobe renal cell carcinoma, collecting duct renal cell carcinoma, granular renal cell carcinoma, mixed granular renal cell carcinoma, renal angiomyolipomas, or spindle renal cell carcinoma), hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma.

In some embodiments the lymphoid neoplasm (e.g., lymphoma) is a B-cell neoplasm. Examples of B-cell neoplasms include, but are not limited to, precursor B-cell neoplasms (e.g., precursor B-lymphoblastic leukemia/lymphoma) and peripheral B-cell neoplasms (e.g., B-cell chronic lymphocytic leukemia/prolymphocytic leukemia/small lymphocytic lymphoma (small lymphocytic (SL) NHL), lymphoplasmacytoid lymphoma/immunocytoma, mantel cell lymphoma, follicle center lymphoma, follicular lymphoma (e.g., cytologic grades: I (small cell), II (mixed small and large cell), III (large cell) and/or subtype: diffuse and predominantly small cell type), low grade/follicular non-Hodgkin's lymphoma (NHL), intermediate grade/follicular NHL, marginal zone B-cell lymphoma (e.g., extranodal (e.g., MALT-type+/−monocytoid B cells) and/or Nodal (e.g., +/−monocytoid B cells)), splenic marginal zone lymphoma (e.g., +/−villous lymphocytes), Hairy cell leukemia, plasmacytoma/plasma cell myeloma (e.g., myeloma and multiple myeloma), diffuse large B-cell lymphoma (e.g., primary mediastinal (thymic) B-cell lymphoma), intermediate grade diffuse NHL, Burkitt's lymphoma, High-grade B-cell lymphoma, Burkitt-like, high grade immunoblastic NHL, high grade lymphoblastic NHL, high grade small non-cleaved cell NHL, bulky disease NHL, AIDS-related lymphoma, and Waldenstrom's macroglobulinemia).

In some embodiments the lymphoid neoplasm (e.g., lymphoma) is a T-cell and/or putative NK-cell neoplasm. Examples of T-cell and/or putative NK-cell neoplasms include, but are not limited to, precursor T-cell neoplasm (precursor T-lymphoblastic lymphoma/leukemia) and peripheral T-cell and NK-cell neoplasms (e.g., T-cell chronic lymphocytic leukemia/prolymphocytic leukemia, and large granular lymphocyte leukemia (LGL) (e.g., T-cell type and/or NK-cell type), cutaneous T-cell lymphoma (e.g., mycosis fungoides/Sezary syndrome), primary T-cell lymphomas unspecified (e.g., cytological categories (e.g., medium-sized cell, mixed medium and large cell), large cell, lymphoepitheloid cell, subtype hepatosplenic γδ T-cell lymphoma, and subcutaneous panniculitic T-cell lymphoma), angioimmunoblastic T-cell lymphoma (AILD), angiocentric lymphoma, intestinal T-cell lymphoma (e.g., +/−enteropathy associated), adult T-cell lymphoma/leukemia (ATL), anaplastic large cell lymphoma (ALCL) (e.g., CD30+, T- and null-cell types), anaplastic large-cell lymphoma, and Hodgkin's lymphoma).

In some embodiments the lymphoid neoplasm (e.g., lymphoma) is Hodgkin's disease. For example, the Hodgkin's disease can be lymphocyte predominance, nodular sclerosis, mixed cellularity, lymphocyte depletion, and/or lymphocyte-rich.

In some embodiments, the cancer is leukemia. In some embodiments, the leukemia is chronic leukemia. Examples of chronic leukemia include, but are not limited to, chronic myelocytic I (granulocytic) leukemia, chronic myelogenous, and chronic lymphocytic leukemia (CLL). In some embodiments, the leukemia is acute leukemia. Examples of acute leukemia include, but are not limited to, acute lymphoblastic leukemia (ALL), acute myeloid leukemia, acute lymphocytic leukemia, and acute myelocytic leukemia (e.g., myeloblastic, promyelocytic, myelomonocytic, monocytic, and erythroleukemia).

In some embodiments, the cancer is liquid tumor or plasmacytoma. Plasmacytoma includes, but is not limited to, myeloma. Myeloma includes, but is not limited to, an extramedullary plasmacytoma, a solitary myeloma, and multiple myeloma. In some embodiments, the plasmacytoma is multiple myeloma.

In some embodiments, the cancer is multiple myeloma. Examples of multiple myeloma include, but are not limited to, IgG multiple myeloma, IgA multiple myeloma, IgD multiple myeloma, IgE multiple myeloma, and nonsecretory multiple myeloma. In some embodiments, the multiple myeloma is IgG multiple myeloma. In some embodiments, the multiple myeloma is IgA multiple myeloma. In some embodiments, the multiple myeloma is a smoldering or indolent multiple myeloma. In some embodiments, the multiple myeloma is progressive multiple myeloma. In some embodiments, multiple myeloma may be resistant to a drug, such as, but not limited to, bortezomib, dexamethasone (Dex-), doxorubicin (Dox-), and melphalan (LR).

B. Methods for Selecting Individuals Who Will Benefit from Telomerase Inhibitor Treatment Provided herein are methods for selecting an individual diagnosed with or suspected of having cancer that will benefit from treatment with a telomerase inhibitor. Telomere length is determined by analyzing the length of telomeric nucleotides in cancer cells present in a biological sample from the individual. By "benefit" it is meant that there is a positive or beneficial difference in the severity or occurrence of at least one clinical or biological score (such as, but not limited to, progression free survival), value, or measure used to evaluate such individuals in those who have been treated with the telomerase inhibitor compounds of the present invention as compared to those that have not.

1. Obtaining Biological Samples

Biological samples from individuals diagnosed with or suspected of having a cell proliferative disorder (such as cancer) can be obtained in various ways. For example, a biological sample can be obtained from a solid tumor, which may be a subcutaneously accessible tumor or from any other type of cancerous solid tumor accessible to biopsy or surgical removal. The biological sample may be obtained by any method known in the art including, but not limited to, needle or core biopsy or fine needle aspiration. Additionally, the biological sample may be fixed, paraffin embedded, fresh, or frozen before telomere length is determined. In some embodiments, the biological sample is formalin fixed and then embedded in paraffin. In some embodiments, the individual has or is suspected of having a blood-borne cancer (i.e., a hematological cancer, such as, but not limited to, leukemia, lymphoma, etc.). In this case, a biological sample may be obtained from the individual's blood.

2. Measuring Telomere Length in Biological Samples

Numerous methods are available in the art for determining telomere length from cells in biological samples according to the methods disclosed herein.

In one aspect, telomere length can be determined by measuring the mean length of a terminal restriction fragment (TRF). The TRF is defined as the length—in general the average length—of fragments resulting from complete digestion of genomic DNA with a restriction enzyme that does not cleave the nucleic acid within the telomeric sequence. Typically, the DNA is digested with restriction enzymes that cleaves frequently within genomic DNA but does not cleave within telomere sequences. Typically, the restriction enzymes have a four base recognition sequence (e.g., AluI, HinfI, RsaI, and Sau3A1) and are used either alone or in combination. The resulting terminal restriction fragment contains both telomeric repeats and subtelomeric DNA. As used herein, subtelomeric DNA are DNA sequences adjacent to tandem repeats of telomeric sequences and contain telomere repeat sequences interspersed with variable telomeric-like sequences. The digested DNA is separated by electrophoresis and blotted onto a support, such as a membrane. The fragments containing telomere sequences are detected by hybridizing a probe, i.e., labeled repeat sequences, to the membrane. Upon visualization of the telomere containing fragments, the mean lengths of terminal restriction fragments can be calculated (Harley, C. B. et al., *Nature*. 345(6274):458-60 (1990), hereby incorporated by reference). TRF estimation by Southern blotting gives a distribution of telomere length in the cells or tissue, and thus the mean telomere length of all cells.

For the various methods described herein, a variety of hybridization conditions may be used, including high, moderate, and low stringency conditions (see, e.g., Sambrook, J. Molecular Cloning: A Laboratory Manual, 3rd Ed., Cold Spring Harbor Laboratory Press, Cold Spring Harbor, N.Y. (2001); Ausubel, F. M. et al., *Current Protocols in Molecular Biology*, John Wiley & Sons (updates to 2002); hereby incorporated by reference). Stringency conditions are sequence-dependent and will be different in different circumstances, including the length of probe or primer, number of mismatches, G/C content, and ionic strength. A guide to hybridization of nucleic acids is provided in Tijssen, P. "Overview of Principles of Hybridization and the Strategy of Nucleic Acid Assays," in *Laboratory Techniques in Biochemistry and Molecular Biology: Hybridization with Nucleic Acid Probes*, Vol 24, Elsevier Publishers, Amsterdam (1993). Generally, stringent conditions are selected to be about 5-10° C. lower than the thermal melting point (i.e., $T_m$) for a specific hybrid at a defined temperature under a defined solution condition at which 50% of the probe or primer is hybridized to the target nucleic acid at equilibrium. Since the degree of stringency is generally determined by the difference in the hybridization temperature and the $T_m$, a particular degree of stringency may be maintained despite changes in solution condition of hybridization as long as the difference in temperature from $T_m$ is maintained. The hybridization conditions may also vary with the type of nucleic acid backbone, for example ribonucleic acid or peptide nucleic acid backbone.

In another aspect, telomere lengths can be measured by flow cytometry (Hultdin, M. et al., *Nucleic Acids Res*. 26: 3651-3656 (1998); Rufer, N. et al., *Nat. Biotechnol*. 16:743-747 (1998); incorporated herein by reference). Flow cytometry methods are variations of FISH techniques. If the starting material is tissue, a cell suspension is made, generally by mechanical separation and/or treatment with proteases. Cells are fixed with a fixative and hybridized with a telomere sequence specific probe, preferably a PNA probe, labeled with a fluorescent label. Following hybridization, cell are washed and then analyzed by FACS. Fluorescence signal is measured for cells in $G_0/G_1$ following appropriate subtraction for background fluorescence. This technique is suitable for rapid estimation of telomere length for large numbers of samples. Similar to TRF, telomere length is the average length of telomeres within the cell.

In other aspects, the average length of telomeres from cells within a biological sample is determined via quantitative PCR (qPCR) or telomere fluorescent in situ hybridization (telo-FISH).

a. qPCR in Formalin Fixed Paraffin Embedded (FFPE) Samples

In some aspects, telomere length is determined using qPCR from DNA extracted from formalin fixed, paraffin embedded (FFPE) biological samples.

In qPCR, a DNA binding dye binds to all double-stranded DNA causing fluorescence of the dye. An increase in DNA product during the PCR reaction leads to an increase in the fluorescence intensity and is measured at each cycle of the PCR reaction. This allows the DNA concentration to be quantified. The relative concentration of the DNA present during the exponential phase of the reaction is determined by plotting the level of fluorescence against the PCR cycle number on a semi-logarithmic scale. A threshold for detection of fluorescence above background is determined. The cycle at which the fluorescence from the sample crosses the threshold is called the cycle threshold (Ct). Because the quantity of DNA theoretically doubles every cycle during the exponential phase, the relative amounts of DNA can be calculated. The baseline is the initial cycles of PCR, in which there is little change in fluorescence signal.

The threshold is a level of ΔRn that is automatically determined by Sequence Detection Systems software or manually set and that is used for Ct determination in real-time assays. The level is set to be above the baseline and sufficiently low to be within the exponential growth region of the amplification curve. The threshold is the line whose intersection with the Amplification plot defines the Ct. Ct is the fractional cycle number at which the fluorescence passed the threshold. The threshold cycle of the sample is determined by subtracting the threshold cycle of a reference sample from the threshold cycle of the telomeric polymerase chain reaction ($\Delta Ct_{sample}=Ct_{telomere}-Ct_{reference}$). The polymerase chain reaction is also performed with primers directed to a single copy number gene as a reference to determine the threshold cycle for the single copy number gene. The average cycle number difference of the single copy gene to the telomeric polymerase chain reaction will determine the telomere lengths ($\Delta Ct=Ct_{telomere}-Ct_{single\ copy\ gene}$).

Telomeric nucleic acids can be extracted from formalin fixed, paraffin embedded biological samples using a mild extraction method. For instance the sample may be treated using detergents, sonication, electroporation, denaturants, etc. to disrupt the cells. The target nucleic acids may be purified as needed. It has been found that mild extraction methods which do not use a column to isolate the nucleic acids are beneficial because these methods retain the smaller fragments of nucleic acid in the final nucleic acid preparation (small DNA fragments are found in FFPE samples and can be lost during column extraction). In some embodiments, the extraction methods retain a majority of the telomeric target nucleic acid fragments that are at least 50 bp, at least 60 bp, at least 70 bp, at least 80 bp. In one embodiment the extraction method retains nucleic acid fragments that are less than 60 bp, that are less than 70 bp, that are less than 80 bp, that are less than 90 bp, that are less than 100 bp, that are less than 110 bp. In one embodiment the mild DNA extraction method does not use a column to isolate the DNA fragments. In one embodiment the nucleic acid extraction method is the BioChain FFPE Tissue DNA extraction kit.

In one embodiment, the FFPE sample can be deparafinated prior to extraction of the DNA.

In another embodiment, the DNA can be extracted from the FFPE sample without prior deparafination of the FFPE sample. In this embodiment the paraffin is not removed from the FFPE sample. In one embodiment, the extracted nucleic acid is heated to at least 88° C., 89° C., 90° C., 91° C., 92° C., 93° C., 94° C., 95° C., 96° C., 97° C. for at least 1 minute, 5 minutes, 10 minutes, 20 minutes, 30 minutes, 40 minutes, 50 minutes, 60 minutes, 70 minutes, 80 minutes.

Following DNA extraction, the DNA is labeled with a fluorescent dye (such as SYBR Green I, Invitrogen, Carlsbad, Calif.). In some embodiments, the DNA is labeled with any of about 0.04×, 0.06×, 0.08×, 0.1×, 0.15×, 0.2×, 0.25×, 0.3×, 0.35×, 0.4×, 0.45×, 0.5×, 0.55×, 0.60×, 0.65×, 0.70×, 0.75×, 0.8×, 0.9×, 1.0×, or 1.1×, inclusive, including any values in between these numbers, SYBR Green I dye. Following DNA labeling, a polymerase chain reaction is performed using a target single copy nucleic acid extracted from the formalin-fixed paraffin biological sample (comprising substantially complementary first and second strands), a first single copy gene primer (wherein the first single copy gene primer is capable of (i) hybridizing to the first strand of the target single copy gene nucleic acid and (ii) being extended by DNA polymerase to form an extended single copy gene primer), and a second single copy gene primer (wherein the second single copy gene primer is capable of (i) hybridizing to the extended first single copy gene primer and/or the target DNA and (ii) being extended by DNA polymerase), and allowing the polymerase chain reaction to proceed in cycles of denaturation and extension and identifying the replication cycle at which the threshold PCR signal is passed.

Telomere sequences are polymerase chain reaction amplified in three stages. Stage 1 is conducted under sufficient conditions to activate the DNA polymerase. Stage 2 is conducted under sufficient conditions to generate PCR products that will act as templates for the subsequence cycles of amplification. In one embodiment, the number of cycles of stage 2 is from 2 to 8 cycles, or from 3 to 6 cycles or from 3 to 5 cycles. In one embodiment, the temperature for dissociation ranges from 90° C. to 98° C., or from 92° C. to 97° C. or from 94° C. to 96° C. for a period from 10 seconds to 20 seconds. In one embodiment, the temperature for association ranges from 45° C. to 60° C., from 49° C. to 58° C., from 50° C. to 55° C. for a period from 5 seconds to 20 seconds. Stage 3 is conducted under sufficient conditions to amplify the templates. In one embodiment, the number of cycles of stage 3 is from 20 to 40 cycles, or from 25 to 35 cycles. In one embodiment, the temperature for dissociation ranges from 90° C. to 98° C., or from 92° C. to 97° C. or from 94° C. to 96° C. for a period from 10 seconds to 20 seconds. In one embodiment, the temperature for association ranges from 45° C. to 70° C., from 49° C. to 68° C., from 50° C. to 60° C. for a period from 5 seconds to 20 seconds.

In one embodiment, the single copy gene amplification qPCR is conducted on a different plate and under different conditions as compared to the telomere amplification qPCR which is conducted on a second plate. In another embodiment, the single copy gene amplification qPCR is conducted in a first well and the telomere amplification qPCR is conducted in a second well on the same plate and under the same conditions. The qPCR telomere analysis may be conducted on from 1, 2 or more tissue samples from the same patient tumor.

In one embodiment the size of the single copy gene amplicon in the PCR reaction is similar to the size of the amplicon for the telomere PCR reaction. In one embodiment, the single gene amplicon generated by the extension of the first and second primers is from about 50 to 100 nucleotides, from 60 to 90 nucleotides, from 70 to 80 nucleotides.

Telomere length is determined by subtracting the threshold cycle of the single gene copy quantitative PCR from the threshold cycle of the telomeric quantitative polymerase chain reaction ($\Delta Ct_{sample} = Ct_{telomere} - Ct_{single\ copy\ gene}$). The average cycle number difference of the single copy gene to the telomeric polymerase chain reaction will determine the telomere lengths ($\Delta Ct = Ct_{telomere} - Ct_{tsingle\ copy\ gene}$). The telomere length is determined for an individual and correlated with telomere length observed in a population of individuals or to a reference individual. In one embodiment, the population of individuals is aged matched with the age of the individual being tested. For humans, the age-matched population is within about 10 years of the age of the individual, or within 5 years or within 1 year. In another embodiment, the population of individuals is matched according to the type of cancer cells (such as, but not limited to, lung cancer, prostate cancer, leukemia, etc.).

Telomere length is expressed as the telomere product normalized by single copy gene product. In other words, relative telomere length of a sample is the factor by which the experimental sample differs from a reference DNA sample in its ratio of telomere repeat copy number to single gene copy number. The quantity of telomere repeats in each experimental sample is measured as the level of dilution of an arbitrarily chosen reference DNA sample that would make the experimental and reference samples equivalent with regard to the number of cycles of PCR needed to generate a given amount of telomere PCR product during the exponential phase of PCR amplification. Similarly the relative quantity of the single copy gene in each experimental sample is expressed as the level of dilution of the reference DNA sample needed to match it to the experimental sample with regard to the number of cycles of PCR needed to generate a given amount of single copy gene PCR product during the exponential phase of the PCR.

In one embodiment, for each experimental sample, the ratio of the dilution factors is the relative telomere to single copy gene (T/S) ratio. Thus T/S=1 when the unknown DNA is identical to the reference DNA in its ratio of telomere repeat copy number to single copy number. The reference DNA sample (to which all of the experimental samples in a given study are compared) can be from a single individual or it can be a pooled sample from multiple individuals or it can be from one or more cell lines having telomeres of known lengths. The T/S ratio of one individual relative to the T/S ratio of the reference individual or the pooled sample or the cell lines corresponds to the relative telomere length of the DNA from the individual. In one embodiment, the cell line is selected from the group consisting of M14Mel-cells, A549 cells, SK-Mel-5 cells, and Ovcar-5 cells.

In another embodiment, for each experimental sample, the ratio of the dilution factors is the $\log_2$ of the single copy gene to relative telomere ($\log_2$ S/T) ratio. The reference DNA sample (to which all of the experimental samples in a given study are compared) can be from a single individual or it can be a pooled sample from multiple individuals or it can be from one or more cell lines having telomeres of known lengths. The $\log_2$ S/T ratio of one individual relative to the $\log_2$ S/T ratio of the reference individual or the pooled sample or the cell lines corresponds to the relative telomere length of the DNA from the individual. In one embodiment, the cell line is selected from the group consisting of M14Mel-cells, A549 cells, SK-Mel-5 cells, and Ovcar-5 cells.

Correlation of the measured telomere length of the individual and the population is examined by various statistical methods, such as survival analysis, including Cox proportional hazard regression models, Kaplan-Meier survival distribution estimate, Peto Wilcoxon test, maximum likelihood analysis, multiple regression analysis and others.

The qPCR methods described herein may also be used to measure an individual's reaction to treatment with a telomerase inhibitor (such as any of the telomerase inhibitors disclosed herein). The rate at which the relative telomere length shortens in solid tumors over the treatment time is measured to determine the reaction of the individual to the telomerase inhibitor.

In addition a variety of agents may be added to the PCR reaction to facilitate optimal hybridization, amplification and detection. These include salts, buffers, neutral proteins, detergents etc. Other agents may be added to improve the efficiency of the reaction such as protease inhibitors, nuclease inhibitors, anti-microbial agents etc.

Further information related to assessing telomere length via qPCR can be found in U.S. Patent Application Publication Nos. 2006/0210980, 2010/0151477, and 2011/0207128 as well as International Patent Application Publication Nos. WO 2010/075413 and WO 2012/0135125, the disclosures of each of which are incorporated by reference herein.

b. Telomere Fluorescent In Situ Hybridization (Telo-FISH)

In some aspects, telomere length is determined using telo-FISH. In this method, cells are fixed and hybridized with a probe conjugated to a fluorescent label, for example, Cy-3, fluoresceine, rhodamine, etc. Probes for this method are oligonucleotides designed to hybridize specifically to telomere sequences. Generally, the probes are 8 or more nucleotides in length, such as 12-20 or more nucleotides in length. In one aspect, the probes are oligonucleotides comprising naturally occurring nucleotides. In one aspect, the probe is a peptide nucleic acid, which has a higher $T_m$ than analogous natural sequences, and thus permits use of more stringent hybridization conditions. Cells may be treated with an agent, such as colcemid, to induce cell cycle arrest at metaphase provide metaphase chromosomes for hybridization and analysis. In some embodiments, cellular DNA can also be stained with the fluorescent dye 4',6-diamidino-2-phenylindole (DAPI).

Digital images of intact metaphase chromosomes are acquired and the fluorescence intensity of probes hybridized to telomeres quantitated. This permits measurement of telomere length of individual chromosomes, in addition to average telomere length in a cell, and avoids problems associated with the presence of subtelomeric DNA (Zjilmans, J. M. et al., *Proc. Natl. Acad Sci. USA* 94:7423-7428 (1997); Blasco, M. A. et al., *Cell* 91:25-34 (1997); incorporated by reference). The intensity of the fluorescent signal correlates with the length of the telomere, with a brighter fluorescent signal indicating a longer telomere.

In some aspects, software (such as the IN Cell developer Toolbox 1.9, GE Corp.) is utilized to quantitate the average telomere length from cells obtained from biological samples and subjected to telo-FISH. In one embodiment, the software is used to draw one or more lines around (i) the cells' nuclei, which is determined based on the location of the DAPI stain, and (ii) around the telomeres. Once each nucleus and telomere is encircled, the software can calculate the intensity of each individual telomere in the cells and thereby determine the average telomere length for the cells derived from the biological sample. In some embodiments, telomere length is calculated using the equation:

$$1.376 \times \log_2(\text{intensity}) - 6.215 \times \sqrt{(\text{area})} \qquad [\text{Equation 1}]$$

where "intensity" is defined as the intensity of the telomere and "area" is defined as the area of the telomere defined by the line drawn around it.

In another embodiment, for each experimental sample, the value calculated using Equation 1 is normalized against the value calculated from a single individual or from a pooled sample from multiple individuals or from one or more cell lines having telomeres of known lengths. The value calculated using Equation 1 relative to the value calculated using Equation 1 from the reference individual or the pooled sample or the cell lines corresponds to the relative telomere length of the DNA from the individual. In one embodiment, the cell line is selected from the group consisting of M14Mel-cells, A549 cells, SK-Mel-5 cells, and Ovcar-5 cells.

Correlation of the measured telomere length of the individual and the population is examined by various statistical methods, such as survival analysis, including Cox proportional hazard regression models, Kaplan-Meier survival distribution estimate, Peto Wilcoxon test, maximum likelihood analysis, multiple regression analysis and others.

3. Selecting an Individual Diagnosed with or Suspected of Having Cancer Who Will Benefit from Treatment with a Telomerase Inhibitor In some aspects, provided herein are methods for selecting an individual diagnosed with or suspected of having cancer who will benefit from treatment with a telomerase inhibitor, the method comprising: determining relative telomere length by analyzing the relative length of telomeric nucleic acids in cancer cells present in a biological sample from the individual; and selecting an individual who will benefit from treatment with a telomerase inhibitor when the average relative telomere length in the cancer cells present in a biological sample from the individual is determined to be in the 50th percentile or less of a relative telomere length range determined from one or more known standards. In some embodiments, the telomerase inhibitor comprises an oligonucleotide. In some embodiments, the telomerase inhibitor is imetelstat. In another embodiment, the cancer is small cell lung cancer, breast cancer, prostate cancer, or a hematological cancer. In still other embodiments, the individual is a human.

Any method can be used to determine relative telomere length in the individual, including any of the methods described herein. In one embodiment, the relative length of telomeric nucleic acids is determined using qPCR from DNA extracted from formalin fixed, paraffin embedded (FFPE) biological samples. When this method is used, the phrase "relative telomere length" is defined as (i) the relative telomere to single copy gene (T/S) ratio or (ii) the log$_2$ of the single copy gene to relative telomere (log$_2$ S/T) ratio. In some embodiments, said one or more known standards are characterized cell lines. By "characterized cell lines" it is meant that the relative length of telomeric nucleic acids of the cells in the cell lines are known and relatively constant. Non-limiting examples of characterized cell lines include M14Mel-cells, A549 cells, SK-Mel-5 cells, and Ovcar-5 cells. In another embodiment, the characterized cell lines are selected from cell lines representative of the biological sample from the individual. Non-limiting examples of these cell lines can include non-small cell lung cancer cell lines, hepatocellular cell lines, or ovarian cell lines. In yet other embodiments, said one of more of the known standards is a telomere length range established from a plurality of naturally occurring tumors from a plurality of individuals. In one embodiment, the cancer cells from a plurality of naturally occurring tumors can be of the same type as the cancer cells present in the biological sample from the individual. In some embodiments, the telomere length in the cancer cells present in the biological sample is determined to be in any of the 45th percentile, 40th percentile, 35th percentile, 30th percentile, 25th percentile, 20th percentile, 15th percentile, 10th percentile, 5th percentile, or less than the telomere length range, inclusive, including any percentiles in between these numbers.

In still other embodiments, relative length of telomeric nucleic acids is determined using qPCR from DNA extracted from formalin fixed, paraffin embedded (FFPE) biological samples and the phrase "relative telomere length" is defined as the log$_2$ of the single copy gene to relative telomere (log$_2$S/T) ratio. In some embodiments, the log$_2$ S/T ratio is less than any of about 0, −0.1, −−0.2, −0.3, −0.4, −0.5, −0.6, −0.7, −0.8, −0.9, −1.0, −1.1, −1.2, −1.3, −1.4, −1.5, −1.6, −1.7, −1.8, −1.9, −2.0, or more.

In another embodiment, the relative length of telomeric nucleic acids is determined using telo-FISH. When this method is used, the phrase "relative telomere length" is defined as the value determined using Equation 1 in the methods described above. In some embodiments, said one or more known standards are characterized cell lines. By "characterized cell lines" it is meant that the relative telomeric nucleic acids of the cells in the cell lines are known and relatively constant. Non-limiting examples of characterized cell lines include M14Mel-cells, A549 cells, SK-Mel-5 cells, and Ovcar-5 cells. In another embodiment, the characterized cell lines are selected from cell lines representative of the biological sample from the individual. Non-limiting examples of these cell lines can include non-small cell lung cancer cell lines, hepatocellular cell lines, or ovarian cell lines. In yet other embodiments, said one of more of the known standards is a telomere length range established from a plurality of naturally occurring tumors from a plurality of individuals. In one embodiment, the cancer cells from a plurality of naturally occurring tumors can be of the same type as the cancer cells present in the biological sample from the individual. In some embodiments, the telomere length in the cancer cells present in the biological sample is determined to be in any of the 45th percentile, 40th percentile, 35th percentile, 30th percentile, 25th percentile, 20th percentile, 15th percentile, 10th percentile, 5th percentile, or less than the telomere length range, inclusive, including any percentiles in between these numbers. In other embodiments, the relative telomere length as determined using Equation 1 in the methods described above is less than any of about 0, −0.1, −0.2, −0.3, −0.4, −0.5, −0.6, −0.7, −0.8, −0.9, −1.0, −1.5, −2.0, −2.5, −3.0, −3.5, −4.0, −4.5, −5.0, −5.5, −6.0, −6.5, −7.0, −7.5, −8.0, −8.5, −9.0, −9.5, −10.0 or more, inclusive, including any number in between these values.

C. Methods of Treating Cell Proliferative Disorders Using Telomerase Inhibitors

In some aspects, the present invention is directed to methods for inhibiting the symptoms or conditions (disabilities, impairments) associated with a cell proliferative disorder (such as cancer) as described in detail above. As such, it is not required that all effects of the condition be entirely prevented or reversed, although the effects of the presently disclosed methods likely extend to a significant therapeutic benefit for the patient. As such, a therapeutic benefit is not necessarily a complete prevention or cure for a particular condition resulting from a cell proliferative disorder (such as cancer), but rather, can encompass a result which includes reducing or preventing the symptoms that result from a cell proliferative disorder, reducing or preventing the occurrence of such symptoms (either quantitatively or qualitatively), reducing the severity of such symptoms or physiological effects thereof, and/or enhancing the recovery of the individual after experiencing a cell proliferative disorder symptoms.

Specifically, a composition of the present invention (such as any of the telomerase inhibitor compounds disclosed herein), when administered to an individual, can treat or prevent one or more of the symptoms or conditions associated with a cell proliferative disorder (such as cancer) and/or reduce or alleviate symptoms of or conditions associated with this disorder. As such, protecting an individual from the effects or symptoms resulting from an a cell proliferative disorder (such as cancer) includes both preventing or reducing the occurrence and/or severity of the effects of the disorder and treating a patient in which the effects of the disorder are already occurring or beginning to occur. A beneficial effect can easily be assessed by one of ordinary skill in the art and/or by a trained clinician who is treating the patient. Preferably, there is a positive or beneficial difference in the severity or occurrence of at least one clinical or biological score, value, or measure used to evaluate such patients in those who have been treated with the methods of the present invention as compared to those that have not.

The methods can be practiced in an adjuvant setting. "Adjuvant setting" refers to a clinical setting in which an individual has had a history of a proliferative disease, particularly cancer, and generally (but not necessarily) been responsive to therapy, which includes, but is not limited to, surgery (such as surgical resection), radiotherapy, and chemotherapy. However, because of their history of the proliferative disease (such as cancer), these individuals are considered at risk of development of the disease. Treatment or administration in the "adjuvant setting" refers to a subsequent mode of treatment. The degree of risk (i.e., when an individual in the adjuvant setting is considered as "high risk" or "low risk") depends upon several factors, most usually the extent of disease when first treated.

The methods provided herein can also be practiced in a "neoadjuvant setting," i.e., the method can be carried out before the primary/definitive therapy. In some embodiments, the individual has previously been treated. In some embodiments, the individual has not previously been treated. In some embodiments, the treatment is a first line therapy.

Accordingly, in some aspects, provided herein are methods for treating an individual diagnosed with or suspected of having cancer, the method comprising: determining relative telomere length by analyzing the relative length of telomeric nucleic acids in cancer cells present in a biological sample from the individual; selecting an individual who will benefit from treatment with a telomerase inhibitor when the average relative telomere length in the cancer cells present in a biological sample from the individual is determined to be in the 50th percentile or less of a relative telomere length range determined from one or more known standards; and administering a therapeutically effective amount of the telomerase inhibitor to the individual. In some embodiments, the telomerase inhibitor comprises an oligonucleotide. In some embodiments, the telomerase inhibitor is imetelstat. In another embodiment, the cancer is small cell lung cancer, breast cancer, prostate cancer, or a hematological cancer. In still other embodiments, the individual is a human.

In other aspects, provided herein are methods for treating an individual diagnosed with or suspected of having cancer, the method comprising: administering a therapeutically effective amount of a telomerase inhibitor to the individual when the average relative telomere length in cancer cells present in a biological sample from the individual has been determined to be in the 50th percentile or less of a relative telomere length range determined from one or more known standards. In some embodiments, the telomerase inhibitor is imetelstat. In another embodiment, the cancer is small cell lung cancer, breast cancer, prostate cancer, or a hematological cancer. In still other embodiments, the individual is a human.

Any method can be used to determine relative telomere length in the individual, including any of the methods described herein. In one embodiment, the relative length of telomeric nucleic acids is determined using qPCR from DNA extracted from formalin fixed, paraffin embedded (FFPE) biological samples. When this method is used, the phrase "relative telomere length" is defined as (i) the relative telomere to single copy gene (T/S) ratio or (ii) $\log_2$ of the single copy gene to relative telomere ($\log_2$S/T) ratio. In some embodiments, said one or more known standards are characterized cell lines. By "characterized cell lines" it is meant that the relative length of telomeric nucleic acids of the cells in the cell lines are known and relatively constant. Non-limiting examples of characterized cell lines include M14Mel-cells, A549 cells, SK-Mel-5 cells, and Ovcar-5 cells. In another embodiment, the characterized cell lines are selected from cell lines representative of the biological sample from the individual. Non-limiting examples of these cell lines can include non-small cell lung cancer cell lines, hepatocellular cell lines, or ovarian cell lines. In yet other embodiments, said one of more of the known standards is a telomere length range established from a plurality of naturally occurring tumors from a plurality of individuals. In one embodiment, the cancer cells from a plurality of naturally occurring tumors can be of the same type as the cancer cells present in the biological sample from the individual. In some embodiments, the telomere length in the cancer cells present in the biological sample is determined to be in any of the 45th percentile, 40th percentile, 35th percentile, 30th percentile, 25th percentile, 20th percentile, 15th percentile, 10th percentile, 5th percentile, or less than the telomere length range, inclusive, including any percentiles in between these numbers.

In another embodiment, the relative length of telomeric nucleic acids is determined using telo-FISH. When this method is used, the phrase "relative telomere length" is defined as the value determined using Equation 1 in the methods described above. In some embodiments, said one or more known standards are characterized cell lines. Non-limiting examples of characterized cell lines include M14Mel-cells, A549 cells, SK-Mel-5 cells, and Ovcar-5 cells. In another embodiment, the characterized cell lines are selected from cell lines representative of the biological sample from the individual. Non-limiting examples of these cell lines can include non-small cell lung cancer cell lines, hepatocellular cell lines, or ovarian cell lines. In yet other embodiments, said one of more of the known standards is a telomere length range established from a plurality of naturally occurring tumors from a plurality of individuals. In one embodiment, the cancer cells from a plurality of naturally occurring tumors can be of the same type as the cancer cells present in the biological sample from the individual. In some embodiments, the telomere length in the cancer cells present in the biological sample is determined to be in any of the 45th percentile, 40th percentile, 35th percentile, 30th percentile, 25th percentile, 20th percentile, 15th percentile, 10th percentile, 5th percentile, or less than the telomere length range, inclusive, including any percentiles in between these numbers.

D. Administration of Telomerase Inhibitors

In some embodiments, the telomerase inhibitor (such as any of the telomerase inhibitor compounds disclosed herein) is administered in the form of an injection. The injection can comprise the compound in combination with an aqueous injectable excipient or carrier. Non-limiting examples of suitable aqueous injectable excipients or carriers are well known to persons of ordinary skill in the art, and they, and the methods of formulating the formulations, may be found in such standard references as Alfonso A R: *Remington's Pharmaceutical Sciences,* 17th ed., Mack Publishing Company, Easton Pa., 1985. Suitable aqueous injectable excipients or carriers include water, aqueous saline solution, aqueous dextrose solution, and the like, optionally containing dissolution enhancers such as 10% mannitol or other sugars, 10% glycine, or other amino acids. The composition can be injected subcutaneously, intraperitoneally, or intravenously.

In some embodiments, intravenous administration is used, and it can be continuous intravenous infusion over a period of a few minutes to an hour or more, such as around fifteen minutes. The amount administered can vary widely depending on the type of the telomerase inhibitor, size of a unit dosage, kind of excipients or carriers, and other factors well known to those of ordinary skill in the art. The telomerase inhibitor can comprise, for example, from about 0.001% to about 10% (w/w), from about 0.01% to about 1%, from about 0.1% to about 0.8%, or any range therein, with the remainder comprising the excipient(s) or carrier(s).

For oral administration, the telomerase inhibitor can take the form of, for example, tablets or capsules prepared by conventional means with pharmaceutically acceptable excipients or carriers such as binding agents; fillers; lubricants; disintegrants; or wetting agents. Liquid preparations for oral administration can take the form of, for example, solutions, syrups or suspensions, or they can be presented as a dry product for constitution with water or other suitable vehicle before use. Such liquid preparations can be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., ationd oil, oily esters, ethyl alcohol or fractionated vegetable oils); and preservatives (e.g., methyl or propyl-p-hydroxybenzoates or sorbic acid). The preparations can also contain buffer salts, flavoring, and coloring as appropriate.

In some embodiments, the telomerase inhibitor can be administered by inhalation through an aerosol spray or a nebulizer that can include a suitable propellant such as, for example, dichlorodifluoromethane, trichlorofluoromethane, dichlorotetrafluoroethane, carbon dioxide, or a combination thereof. In one non-limiting example, a dosage unit for a pressurized aerosol can be delivered through a metering valve. In another embodiment, capsules and cartridges of gelatin, for example, can be used in an inhaler and can be formulated to contain a powderized mix of the compound with a suitable powder base such as, for example, starch or lactose.

In some embodiments, the amount of telomerase inhibitor in the composition (such as a pharmaceutical composition) is included in any of the following ranges: about 0.5 to about 5 mg, about 5 to about 10 mg, about 10 to about 15 mg, about 15 to about 20 mg, about 20 to about 25 mg, about 20 to about 50 mg, about 25 to about 50 mg, about 50 to about 75 mg, about 50 to about 100 mg, about 75 to about 100 mg, about 100 to about 125 mg, about 125 to about 150 mg, about 150 to about 175 mg, about 175 to about 200 mg, about 200 to about 225 mg, about 225 to about 250 mg, about 250 to about 300 mg, about 300 to about 350 mg, about 350 to about 400 mg, about 400 to about 450 mg, or about 450 to about 500 mg. In some embodiments, the amount of a telomerase inhibitor in the effective amount of the pharmaceutical composition (e.g., a unit dosage form) is in the range of about 5 mg to about 500 mg, such as about 30 mg to about 300 mg or about 50 mg to about 200 mg. In some embodiments, the concentration of the telomerase inhibitor in the pharmaceutical composition is dilute (about 0.1 mg/ml) or concentrated (about 100 mg/ml), including for example any of about 0.1 to about 50 mg/ml, about 0.1 to about 20 mg/ml, about 1 to about 10 mg/ml, about 2 mg/ml to about 8 mg/ml, about 4 to about 6 mg/ml, about 5 mg/ml. In some embodiments, the concentration of the telomerase inhibitor is at least about any of 0.5 mg/ml, 1.3 mg/ml, 1.5 mg/ml, 2 mg/ml, 3 mg/ml, 4 mg/ml, 5 mg/ml, 6 mg/ml, 7 mg/ml, 8 mg/ml, 9 mg/ml, 10 mg/ml, 15 mg/ml, 20 mg/ml, 25 mg/ml, 30 mg/ml, 40 mg/ml, or 50 mg/ml.

Exemplary effective amounts of a telomerase inhibitor in the pharmaceutical composition include, but are not limited to, at least about any of 25 mg/m$^2$, 30 mg/m$^2$, 50 mg/m$^2$, 60 mg/m$^2$, 75 mg/m$^2$, 80 mg/m$^2$, 90 mg/m$^2$, 100 mg/m$^2$, 120 mg/m$^2$, 125 mg/m$^2$, 150 mg/m$^2$, 160 mg/m$^2$, 175 mg/m$^2$, 180 mg/m$^2$, 200 mg/m$^2$, 210 mg/m$^2$, 220 mg/m$^2$, 250 mg/m$^2$, 260 mg/m$^2$, 300 mg/m$^2$, 350 mg/m$^2$, 400 mg/m$^2$, 500 mg/m$^2$, 540 mg/m$^2$, 750 mg/m$^2$, 1000 mg/m$^2$, or 1080 mg/m$^2$. In various embodiments, the pharmaceutical composition includes less than about any of 350 mg/m2, 300 mg/m$^2$, 250 mg/m$^2$, 200 mg/m$^2$, 150 mg/m$^2$, 120 mg/m$^2$, 100 mg/m$^2$, 90 mg/m$^2$, 50 mg/m$^2$, or 30 mg/m$^2$ of a telomerase inhibitor. In some embodiments, the amount of the telomerase inhibitor per administration is less than about any of 25 mg/m$^2$, 22 mg/m$^2$, 20 mg/m$^2$, 18 mg/m$^2$, 15 mg/m$^2$, 14 mg/m$^2$, 13 mg/m$^2$, 12 mg/m$^2$, 11 mg/m$^2$, 10 mg/m$^2$, 9 mg/m$^2$, 8 mg/m$^2$, 7 mg/m$^2$, 6 mg/m$^2$, 5 mg/m$^2$, 4 mg/m$^2$, 3 mg/m$^2$, 2 mg/m$^2$, or 1 mg/m$^2$. In some embodiments, the effective amount of a telomerase inhibitor in the pharmaceutical composition is included in any of the following ranges: about 1 to about 5 mg/m$^2$, about 5 to about 10 mg/m$^2$, about 10 to about 25 mg/m$^2$, about 25 to about 50 mg/m$^2$, about 50 to about 75 mg/m$^2$, about 75 to about 100 mg/m$^2$, about 100 to about 125 mg/m$^2$, about 125 to about 150 mg/m$^2$, about 150 to about 175 mg/m$^2$, about 175 to about 200 mg/m$^2$, about 200 to about 225 mg/m$^2$, about 225 to about 250 mg/m$^2$, about 250 to about 300 mg/m$^2$, about 300 to about 350 mg/m$^2$, or about 350 to about 400 mg/m$^2$. In some embodiments, the effective amount of a telomerase inhibitor in the pharmaceutical composition is about 5 to about 300 mg/m$^2$, such as about 20 to about 300 mg/m$^2$, about 50 to about 250 mg/m$^2$, about 100 to about 150 mg/m$^2$, about 120 mg/m$^2$, about 130 mg/m$^2$, or about 140 mg/m$^2$, or about 260 mg/m$^2$.

In some embodiments of any of the above aspects, the effective amount of a telomerase inhibitor in the pharmaceutical composition includes at least about any of 1 mg/kg, 2.5 mg/kg, 3.5 mg/kg, 5 mg/kg, 6.5 mg/kg, 7.5 mg/kg, 9.4 mg/kg, 10 mg/kg, 15 mg/kg, or 20 mg/kg. In various embodiments, the effective amount of a telomerase inhibitor in the pharmaceutical composition includes less than about any of 350 mg/kg, 300 mg/kg, 250 mg/kg, 200 mg/kg, 150 mg/kg, 100 mg/kg, 50 mg/kg, 30 mg/kg, 25 mg/kg, 20 mg/kg, 10 mg/kg, 9.4 mg/kg, 7.5 mg/kg, 6.5 mg/kg, 5 mg/kg, 3.5 mg/kg, 2.5 mg/kg, or 1 mg/kg of a telomerase inhibitor.

Exemplary dosing frequencies for the pharmaceutical compositions (such as a pharmaceutical composition containing any of the telomerase inhibitors disclosed herein) include, but are not limited to, daily; every other day; twice per week; three times per week; weekly without break; weekly, three out of four weeks; once every three weeks; once every two weeks; weekly, two out of three weeks. In some embodiments, the pharmaceutical composition is administered about once every 2 weeks, once every 3 weeks, once every 4 weeks, once every 6 weeks, or once every 8 weeks. In some embodiments, the composition is administered at least about any of 1×, 2×, 3×, 4×, 5×, 6×, or 7× (i.e., daily) a week, or three times daily, two times daily. In some embodiments, the intervals between each administration are less than about any of 6 months, 3 months, 1 month, 20 days, 15 days, 12 days, 10 days, 9 days, 8 days, 7 days, 6 days, 5 days, 4 days, 3 days, 2 days, or 1 day. In some embodiments, the intervals between each administration are more than about any of 1 month, 2 months, 3 months, 4 months, 5 months, 6 months, 8 months, or 12 months. In some embodiments, there is no break in the dosing schedule. In some embodiments, the interval between each administration is no more than about a week.

The administration of the pharmaceutical composition can be extended over an extended period of time, such as from about a month up to about seven years. In some embodiments, the composition is administered over a period of at least about any of 2, 3, 4, 5, 6, 7, 8, 9, 10, 11, 12, 18, 24, 30, 36, 48, 60, 72, or 84 months.

EXAMPLES

Example 1: Preparation and Lipid Conjugation of Oligonucleotide N3'→P5' Phosphoramidates (NP) or N3'→P5' Thiophosphoramidates (NPS)

This example shows how to synthesize lipid conjugated Oligonucleotide N3'→P5' Phosphoramidates (NP) or N3'→P5' Thiophosphoramidates (NPS).

Materials and Methods

Starting Compounds

These compounds may be prepared as described, for example, in McCurdy et al., *Tetrahedron Letters* 38: 207-210 (1997) or Pongracz & Gryaznov, *Tetrahedron Letters* 49: 7661-7664 (1999). The starting 3'-amino nucleoside monomers may be prepared as described in Nelson et al., *J. Org. Chem.* 62: 7278-7287 (1997) or by the methods described in Gryaznov et al., US Application Publication No. 2006/0009636.

Lipid Attachment

A variety of synthetic approaches can be used to conjugate a lipid moiety L to the oligonucleotide, depending on the nature of the linkage selected; see, for example, Mishra et al., *Biochim. et Biophys. Acta* 1264: 229-237 (1995), Shea et al., *Nucleic Acids Res.* 18: 3777-3783 (1995), or Rump et al., *Bioconj. Chem.* 9: 341-349 (1995). Typically, conjugation is achieved through the use of a suitable functional group at an oligonucleotide terminus. For example, the 3'-amino group present at the 3'-terminus of the NP and NPS oligonucleotides can be reacted with carboxylic acids, acid chlorides, anhydrides and active esters, using suitable coupling catalysts, to form an amide linkage. Thiol groups are also suitable as functional groups (see Kupihar et al., *Bioorg. Med. Chem.* 9: 1241-1247 (2001)). Various amino- and thiol-functionalized modifiers of different chain lengths are commercially available for oligonucleotide synthesis.

Specific approaches for attaching lipid groups to a terminus of an NP or NPS oligonucleotide include those described in US Application Publication No. 2005/0113325, which is incorporated herein in its entirety by reference. In addition to the amide linkages noted above, for example, lipids may also be attached to the oligonucleotide chain using a phosphoramidite derivative of the lipid, to produce a phosphoramidate or thiophosphoramidate linkage connecting the lipid and the oligonucleotide. The free 3'-amino of the fully protected support-bound oligonucleotide may also be reacted with a suitable lipid aldehyde, followed by reduction with sodium cyanoborohydride, which produces an amine linkage.

For attachment of a lipid to the 5' terminus, as also described in US Application Publication No. 2005/0113325, the oligonucleotide can be synthesized using a modified, lipid-containing solid support. Reaction of 3'-amino-1,2-propanediol with a fatty acyl chloride (RC(O)Cl), followed by dimethoxytritylation of the primary alcohol and succinylation of the secondary alcohol, provides an intermediate which is then coupled, via the free succinyl carboxyl group, to the solid support. An example of a modified support is shown below, where S— represents a long chain alkyl amine CPG support, and R represents a lipid.

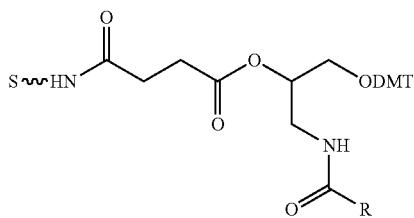

This procedure is followed by synthesis of the oligonucleotide in the 5' to 3' direction, as described, for example, in Pongracz & Gryaznov (1999), starting with deprotection and phosphitylation of the —ODMT group. This is effective to produce, for example, the following structure, after cleavage from the solid support:

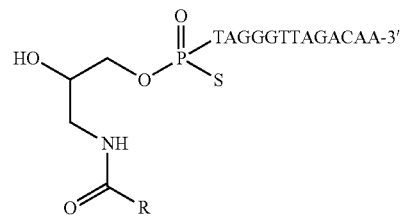

The structure above, when —R is —$(CH_2)_{14}CH_3$ (palmitoyl), is designated herein as GRN163L (Imetelstat).

FlashPlate™ Assay

This assay was carried out essentially as described in Asai et al., *Cancer Research* 63: 3931-3939 (2003). Briefly, the assay detects and/or measures telomerase activity by measuring the addition of TTAGGG telomeric repeats to a biotinylated telomerase substrate primer. The biotinylated products are captures on streptavidin-coated microtiter plates, and an oligonucleotide probe complementary to 3.5 telomere repeats, labeled with 33P, is used for measuring telomerase products. Unbound probe is removed by washing, and the amount of probe annealing to the captured telomerase products is determined by scintillation counting.

Example 2: qPCR on Formalin-Fixed, Paraffin-Embedded Samples from Imetelstat NSC Phase II (CP14B-012) Study This example demonstrates the performance of the quantitative polymerase chain reaction for determining the relative telomere length of FFPE NSC Phase II (CP14B-012) Study tissue samples.

Materials and Methods

Clinical Trial Design

The purpose of the NSC Phase II (CP14B-012) Study was to evaluate the efficacy and safety of imetelstat (GRN163L) as maintenance therapy for patients with advanced stage non-small cell lung cancer who have not progressed after 4 cycles of platinum based therapy. Participants were randomized in a 2:1 ratio to imetelstat plus standard of care versus standard of care alone. Participants who received bevacizumab with their induction chemotherapy continued to receive bevacizumab in this study.

The primary outcome measures were progression-free survival, defined as the time from randomization to documented disease progression or death, whichever occurred earlier, as determined by the investigator's assessment according to RECIST (Response Evaluation Criteria in Solid Tumors). The secondary outcome measures were objective response, time to all-cause mortality, and safety and tolerability (assessed by the incidence, nature, and severity of adverse events, laboratory abnormalities, and vital signs.

The patients were divided into two arms. In the experimental arm, patients received Imetelstat plus the standard of care (Bevacizumab or observation). Specifically, 9.4 mg/kg of Imetelstat (GRN163L) was given to patients over a 2 hour IV infusion on Day 1 and Day 8 of each 21 day cycle until disease progression. If administered, Bevacizumab was given on Day 1 of each 21-day cycle, with dosage and duration according to the FDA-approved Bevacizumab package insert.

In the control arm, patients received Bevacizumab or observation. If administered, Bevacizumab was given on Day 1 of each 21-day cycle, with dosage and duration according to the FDA-approved Bevacizumab package insert.

Samples were obtained from 61 of the 116 patients enrolled in the NSC Phase II (CP14B-012) Study, and of these, 57 resulted in evaluable assay results used for the progression-free survival (PFS) analysis.

Formalin Fixation and Paraffin Embedding

Formalin-fixed and paraffin embedded samples were prepared using the HistoGel Kit (catalog #R904012: Richard Allen Scientific, a subsidiary of ThermoFisher, Kalamazoo, Mich.). Cells were cultured to 80-90% confluence. Cell pellets ($10^6$/pellet) were first gently mixed in 200-500 μL of HistoGel melted at 50±5° C., then cooled on ice to solidify. After solidification, samples were quickly spun to remove the residual liquid. Ten mL of 4% formalin was added to the gelled pellets and the cell pellets were fixed for 48 hours at room temperature. Fixed cell pellets were then embedded using standard histology technique at Histo-Tec Laboratory in Hayward, Calif. and then frozen at −80° C.

DNA Extraction

Genomic DNA of the NSCLC Phase II Study samples was isolated from FFPE processed samples using the FFPE DNA Extraction Kit made by BioChain (BioChain Institute, catalog #K5019100, Hayward, Calif.), according to the manufacturer's instructions. The tissue was mixed in 170 μL of kit buffer and 30 μL of proteinase K. The mixture was incubated at 56° C. for one hour, then the temperature was increased to 90° C. for 60 minutes and then 98° C. for 2 minutes and placed on ice for 2 minutes. The mixture was centrifuged at 14,000 rpm for 10 minutes at 4° C. and the supernatant obtained. DNA concentration was determined by Quant-iT Pico Green dsDNA Assay Kit (Invitrogen, catalog #P7589, Carlsbad, Calif.). The concentration of DNA in the supernatant was adjusted to 0.1 ng/μL with $H_2O$.

Quantitative PCR (qPCR)

All quantitative PCR reactions were carried out using ABI Prism 7900 HT Sequence Detection System (Applied Biosystems, Carlsbad Calif.). Two PCRs were performed for each sample, one to determine the cycles threshold (Ct) value for telomere (T) amplification and the other to determine the Ct value for the amplification of a single copy gene (acidic ribosomal phosphoprotein P, 36B4).

The primer sequences for telomere amplification were Telg 5'-ACA CTA AGG TTT GGG TTT GGG TTT GGG TTT GGG TTA GTG T (SEQ ID NO:4) and Telc 5'-TGT TAG GTA TCC CTA TCC CTA TCC CTA TCC CTA TCC CTA ACA (SEQ ID NO:5) (Cawthon, 2009); and those for 36B4u: 5'-CAG CAA GTG GGA AGG TGT AAT CC (SEQ ID NO:6) and 36B4d: 5'-CCC ATT CTA TCA TCA ACG GGT ACA A (SEQ ID NO:7) (Cawthon, 2002).

Each PCR reaction for telomere amplification was performed using 1 ng/10 μL sample (0.1 ng/μL) and a 40 μL PCR mixture containing 1.25 U Hotstart DNA Taq polymerase (BioChain), 150 nM 6-ROX fluorescent dye, 0.04× SYBR Green I nucleic acid stain (Invitrogen, Carlsbad Calif.), 50 mM KCl, 2 mM $MgCl_2$, 0.2 mM of each deoxynucleoside triphosphates (Applied Biosystems, Carlsbad, Calif.), 5 mM dithiothreitol, 1% dimethyl sulfoxide, and 15 mM Tris-HCl pH 8.0 and primer pair Telg and Telc (both at 900 nM). The higher primer concentration is preferred for the telomeric DNA when using FFPE DNA, because high concentrations of primers allow multiple annealing sites.

Telomere sequences were amplified in three stages. Stage 1: 95° C. for 10 minutes to activate the Hotstart DNA Taq polymerase (BioChain); stage 2: 5 cycles of 15 s at 95° C., 10 s at 50° C. to generate PCR products that will act as templates for the subsequent cycles of amplification. The annealing temperature at stage 2 could range from 49° C. to 58° C. Stage 3: 25 cycles of 15 s at 95° C., 15 s at 60° C. with signal acquisition at 60° C. Total running time was 70 minutes.

Amplification of the single copy 36B4 gene was conducted using Power SYBR Green PCR Master Mix (Applied Biosystems) as follows: Ten minutes at 95° C. to activate the DNA polymerase in the Master Mix (Applied Biosystems), followed by 40 cycles of 15 s at 95° C., 1 minute at 58° C. with signal acquisition at 58° C. The 36B4 amplification was performed using 1 ng/10 μL of samples (0.1 ng/μL), 40 μL of Power SYBR Green Master Mix (Applied Biosystems, Carlsbad Calif.) and primer pair 36B4d (300 nM) and 36B4u (300 nM).

The number of cycles for telomere sequence PCR at stage 2 was modified to 5 cycles in order to have proper ΔCt value ($\Delta Ct_{sample} = Ct_{telomere} - Ct_{reference}$) when using 1 ng of DNA in each PCR reaction. 1 ng-10 ng of DNA per reaction had >94% PCR efficiency in the reproducibility studies. The cycle number for the single copy gene PCR needs to be nine cycles higher than that for the telomere PCR in order to produce sufficient single copy gene PCR product.

The average cycle number differences of single copy gene to telomere ($Ct_{36B4} - Ct_{telomere}$, or ΔCt) among the samples ranged from 9.208 to 14.500.

DNA crosslinking and fragmentation in genomic DNA from FFPE samples pose a unique challenge, especially for amplifying long, repetitive telomeric sequences, while amplification of a 76 bp fragment of a single copy gene for acid ribosomal phosphoprotein P (designated 36B4 in this document) in the same sample is often unaffected. To solve this problem, several PCR conditions were altered, i.e. the choice of the PCR primers, the PCR reaction buffer conditions and the thermal cycling conditions, to achieve the goal of shortening the telomere amplicon size and improving the PCR amplification efficiency.

Results

Figure 3A:
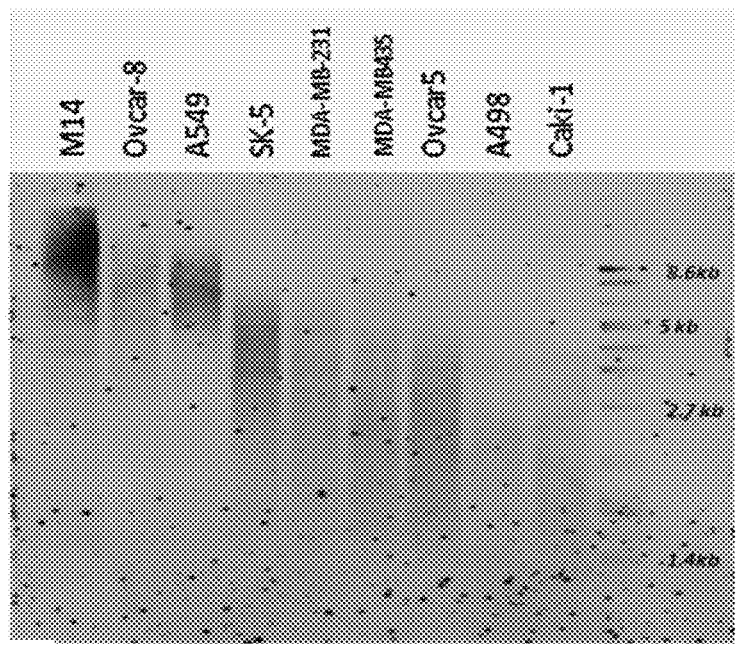
FIG. 3A depicts terminal restriction fragment (TRF) length in human formalin-fixed paraffin-embedded (FFPE) tumor cell lines M14Mel, OVCAR-8, A549, SK-Mel-5, MDA-MB-231, MDA-MB435, OVCAR-5, A498 and CAKI-1, as determined by Southern Blotting.
Figure 3B:
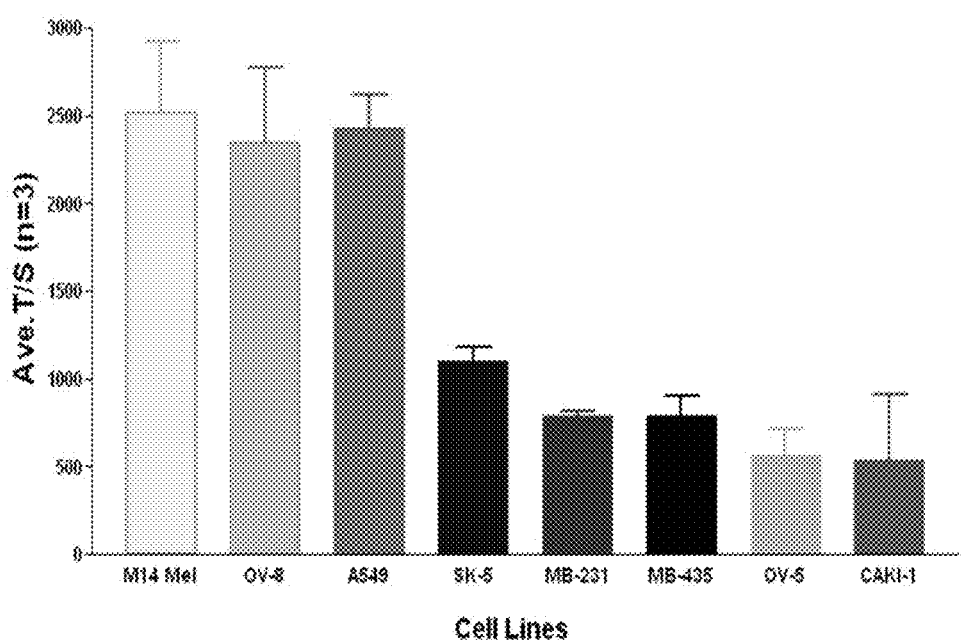
FIG. 3B depicts average T/S ratios in human formalin-fixed paraffin-embedded (FFPE) tumor cell lines M14Mel, OVCAR-8, A549, SK-Mel-5, MDA-MB-231, MDA-MB435, OVCAR-5, A498 and Caki-1 as determined by quantitative PCR (qPCR).

Average telomere lengths in human tumor cell lines determined by Southern blot correlate with results obtained by qPCR (assay standards) (FIGS. 3A and 3B).

Figure 1B:
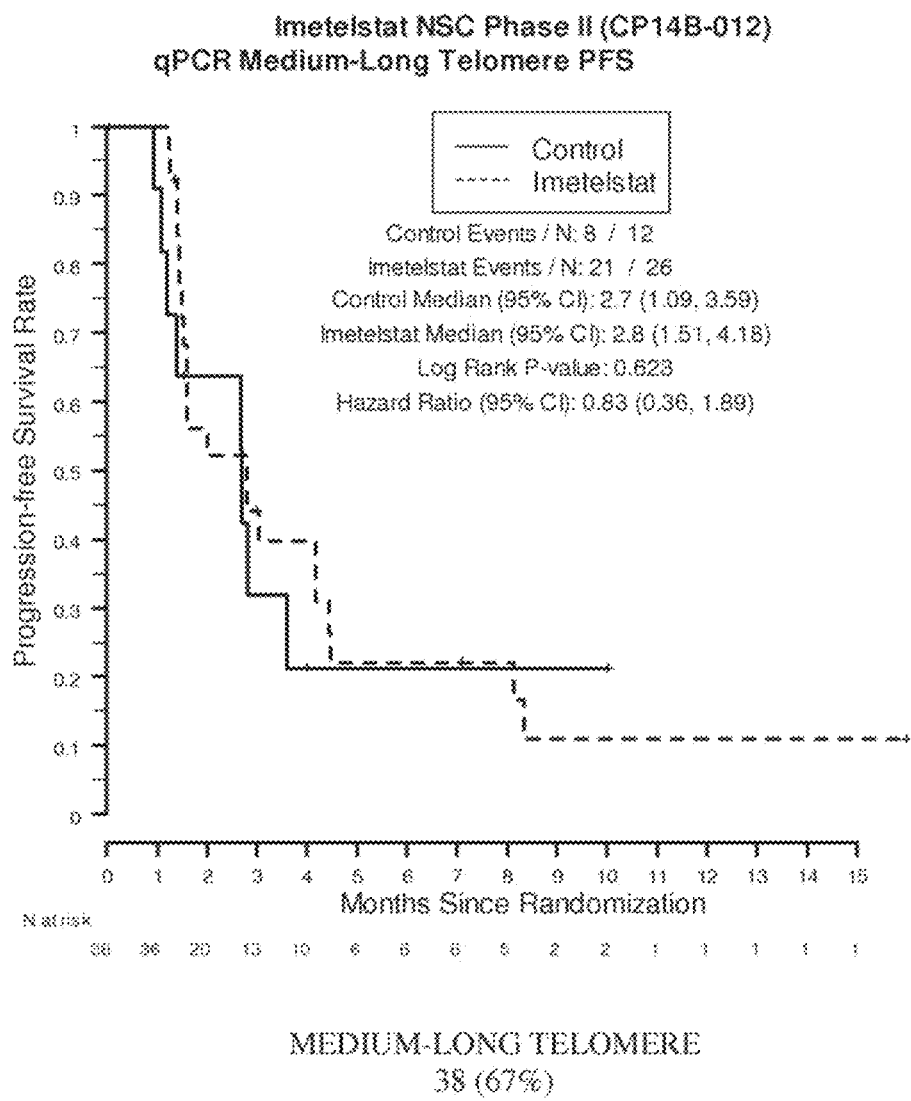
FIG. 1B depicts the progression-free survival (PFS) analysis of the medium-long telomere subgroup (longer 67% of relative telomere length) of the Imetelstat Non-Small Cell (NSC) Lung Cancer Phase II (CP14B-012) Study based on average telomere lengths determined using quantitative PCR (qPCR) as shown in Example 2.

Analysis of progression-free survival in telomere length subgroups obtained by qPCR indicated patients with short telomeres who were treated with Imetelstat were significantly more responsive compared to controls than patients with medium-long telomeres (FIGS. 1A and 1B).

19 out of the 57 samples (33%) had short telomeres (FIG. 1A). For these, the progression-free survival analysis indicated the following: control events/N were 7/8, and Imetelstat events/N were 8/11 (FIG. 1A); the control median (95% CI) was 1.48 (1.18, 2.76), and the Imetelstat median (95% CI) was 4.05 (1.25, NA) (FIG. 1A); the log rank P-value was 0.042, and the hazard ratio (95% CI) was 0.32 (0.1, 1.02) (FIG. 1A).

38 out of the 57 samples (67%) had medium-long telomeres (FIG. 1B). For these, the progression-free survival analysis indicated the following: control events/N were 8/12, and Imetelstat events/N were 21/26 (FIG. 1B); the control median (95% CI) was 2.7 (1.09, 3.59), and the Imetelstat median (95% CI) was 2.8 (1.51, 4.18) (FIG. 1B); the log rank P-value was 0.623, and the hazard ratio (95% CI) was 0.83 (0.36, 1.89) (FIG. 1B).

Figure 5:
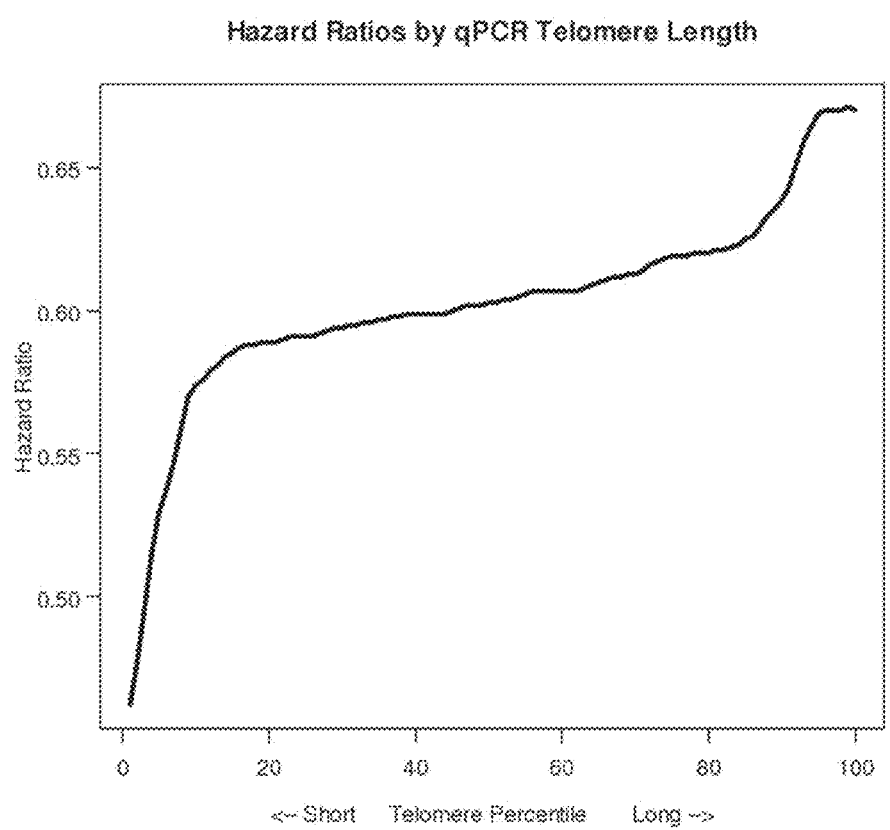
FIG. 5 depicts progression free survival (PFS) hazard ratios (HR) for patients from the Imetelstat Non-Small Cell (NSC) Lung Cancer Phase II (CP14B-012) Study plotted against patient telomere length percentiles, where the relative telomere length was determined by quantitative PCR (qPCR).

Treatment effect increases in a non-linear fashion with reducing tumor telomere length (FIG. 5).

Example 3: Telo-FISH on Formalin-Fixed Paraffin-Embedded Samples from NSC Phase II (CP14B) Study Samples were obtained from 61 of the 116 patients enrolled in the NSC Phase II (CP14B-012) Study described above. Of these 61 patient samples, 59 resulted in evaluable Telo-FISH assay results used for PFS analysis. Each assay produced data for between 7 and 14545 foci from six regions ('fields') on a slide. The area and fluorescent intensity were recorded for each of the foci.

Materials and Methods

Unstained FFPE tissue slides (5 μm thick tissue sections) were prepared by routine histological methods. The tissue slides were preheated at 65° C. for 6 minutes to melt the paraffin, then loaded onto a slide rack. The loaded slide rack was immersed in 100 mL of xylene in a staining tank for 3 minutes two times (3 minutes×2) to remove paraffin.

The slides were then hydrated in 3-minute increments through a graded ethanol series: 100% EtOH, (3 minutes×2), 95% EtOH (3 minutes×2), and 70% EtOH (3 minutes×2). After this ethanol immersion, the slides were immersed in de-ionized water for 3 minutes and in de-ionized water with 1% Tween-20 detergent for another 3 minutes.

The slides were dipped briefly into water to wash off the Tween-20, then blotted and immersed into a 100 mL 1× citrate buffer tank containing Vector target unmasking solution (100× dilution into $H_2O$). The whole tank was placed in a pre-heated (boiling) steamer and steamed for 35 minutes, then removed from the steamer and cooled for at least 30 minutes at room temperature. The slides were next immersed in de-ionized water for 3 minutes, then 70% ethanol twice, 95% ethanol twice, and air dried.

A hybridization probe was prepared using the following reagents and volumes:

| Hybridization buffer for PNA telomere probe | | |
|---|---|---|
| reagent | volume | common |
| distilled H2O | 190 ul | |
| 1M Tris HCl (pH 7.5) | 10 ul | 1:2 dilution from 2M Tris•HCl |
| Bloking buffer | 5 ul (1x) | (dry milk in Maleic acid, 10% stock) |
| 100% Formamide | 700 ul | |

10 ug/mL PNA telomere probe TelC-Cy3 (PNA Bio Inc.) CCCTAACCCTAACCCTAA (SEQ ID NO:8) stock was diluted in hybridization buffer with a proper dilution factor (e.g. 5×). 30-50 μL of diluted PNA probe was added onto the specimen, and then a cover slip applied without introducing air bubbles. The slides were placed on the surface of a slide incubator for 6 minutes at 84° C. to denature the telomere DNA.

The slides were moved to a dark closed container and hybridized for 2 hours at room temperature. The container was moistened either by adding water or a wet kimwipe to prevent desiccation.

The wash buffer for PNA telomere probe was prepared using the following reagents and volumes:

| Wash buffer for PNA telomere probe (100 ml) | | |
|---|---|---|
| reagent | volume | common |
| distilled H2O | 29 ml | |
| 1M Tris HCl (pH7.5) | 1 ml | 1:2 dilution from 2M Tris•HCl |
| 100% Formamide | 700 ml | |

After removal of the cover slips, the slides were washed with PNA wash buffer for 15 minutes two times (15 minutes×2) with gentle agitation at room temperature. Next the slides were drained and the nuclei counter stained with 1 ug/ml DAPI solution for 5 minutes (1:5000 dilution in water of a 5 mg/mL DAPI stock solution; e.g., 20 μL of 5 mg/mL DAPI stock in 100 mL of $H_2O$).

The slides were next washed in distilled water for 3 minutes four times (3 minutes×4), then drained and air dried. Cover slips were mounted on the slides using anti-fade mounting media solution while avoiding air bubbles. Mounted slides were kept overnight in a dark place to protect the slides from light before testing under the microscope. Stained slides were screened under IN Cell Analyzer 2000 (GE Corp.) to collect the fluorescent signal intensity and fluorescent signal area of DAPI (nuclei) and Cy3 (telomere).

The IN Cell developer Toolbox 1.9 (GE Corp.) was utilized to quantitate the average telomere length from cells obtained from biological samples and subjected to telo-FISH. This software was used to draw lines around cell nuclei based on the location of the DAPI stain, and around cell telomeres based on the location of the telomere-specific fluorescence. Once each nucleus and telomere was encircled, the software calculated the intensity and the area of each individual telomere in the cells and determined the average telomere length for the cells derived from the biological sample according to Equation 1:

$$1.376 \times \log_2(\text{intensity}) - 6.215 \times \sqrt{(\text{area})} \qquad [\text{Equation 1}].$$

Results

Figure 4A:
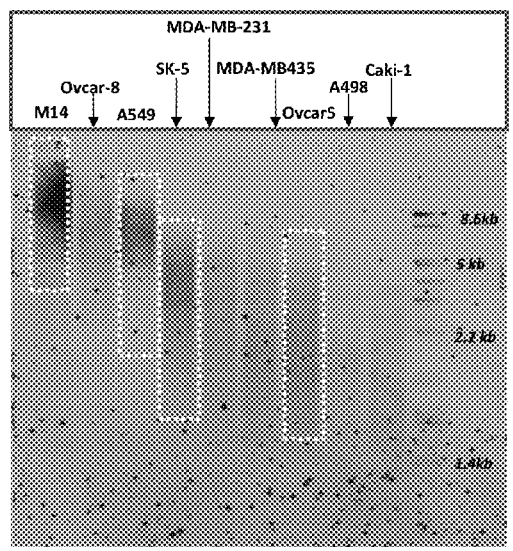
FIG. 4A depicts terminal restriction fragment (TRF) length in human formalin-fixed paraffin-embedded (FFPE) tumor cell lines M14Mel, OVCAR-8, A549, SK-Mel-5, MDA-MB-231, MDA-MB435, OVCAR-5, A498 and CAKI-1, as determined by Southern Blotting.
Figure 4B:
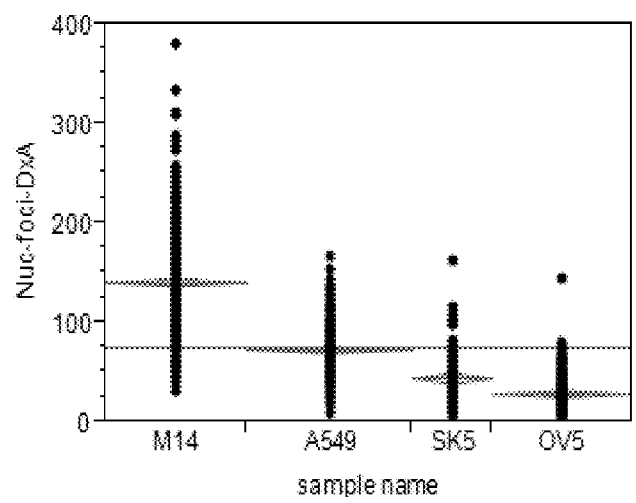
FIG. 4B depicts Telo-FISH results for human cell lines M14Mel, A549, SK-Mel-5, and OVCAR-5 (OV5).

Telomere lengths in human tumor cell lines determined by Southern blot correlate with results obtained by telo-FISH (assay standards) (FIGS. 4A and 4B).

Figure 2:
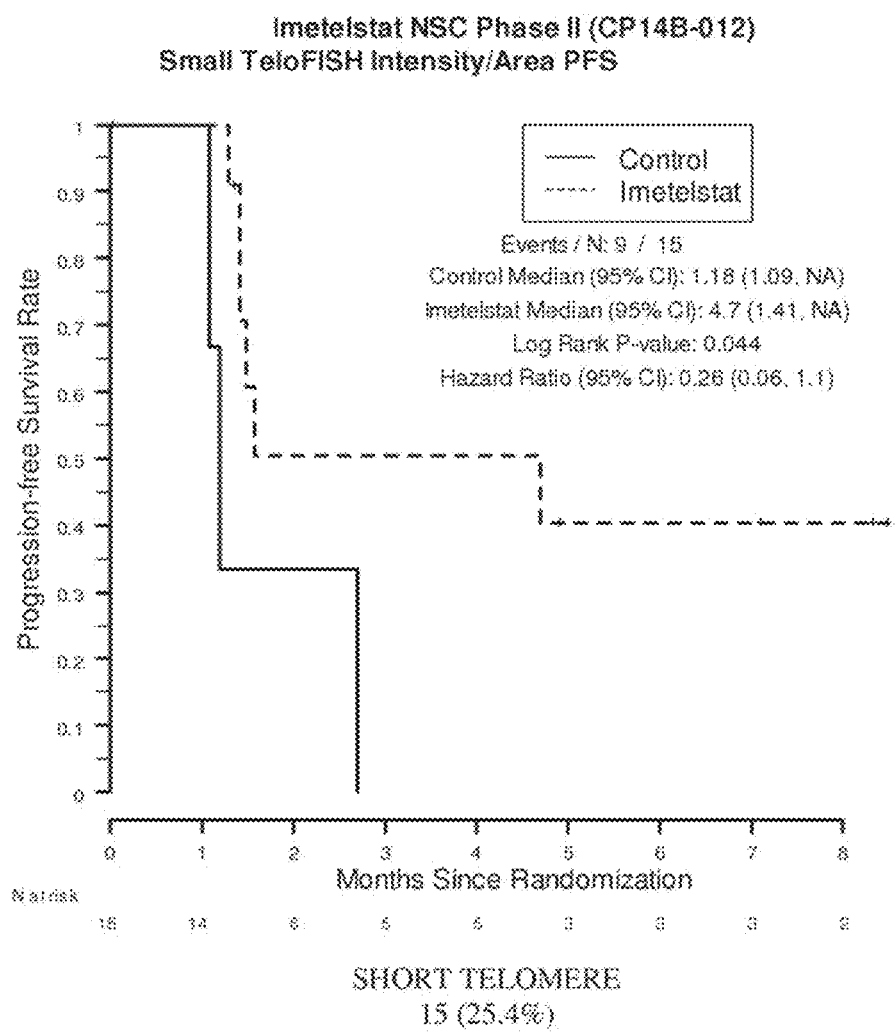
FIG. 2 depicts the progression-free survival (PFS) analysis of data from the 15 patients in the Imetelstat-treated arm of the Imetelstat Non-Small Cell (NSC) Lung Cancer Phase II (CP14B-012) Study having the shortest $25^{th}$ percentile of relative telomere lengths. Analysis of these patients' individual telomere lengths was done using Telomere Fluorescent In Situ Hybridization (Telo-FISH).

Analysis of progression-free survival in telomere length subgroups obtained by Telo-FISH IN Cell-Quartile Split indicated large area and low intensity (i.e., a low intensity to area ratio) are associated with better Imetelstat efficacy (FIG. 2).

Progression-free survival analysis indicated the following: Events/N were 9/15; the control median (95% CI) was 1.18 (1.09, NA), and the Imetelstat median (95% CI) was 4.7 (1.41, NA) (FIG. 2); the log rank P-value was 0.044, and the hazard ratio (95% CI) was 0.26 (0.06, 1.1) (FIG. 2).

Telo-FISH multivariate predication of progression-free survival in imetelstat treated patients resulted in the following data:

| TeloFISH Metric | Hazard Ratio (HR) | Linear Coefficient Log (HR) | P-value |
|---|---|---|---|
| Log2 (Intensity) | 3.960 | 1.376 | 0.22 |
| Square root (Area) | 0.002 | −6.215 | 0.017 |

Quartile Split of PFS Risk From Multivariate Model (Small Intensity/Area Ratio):

| Small Intensity/Area |
| --- |
| 15/59 (25.4%) |

Figure 6:
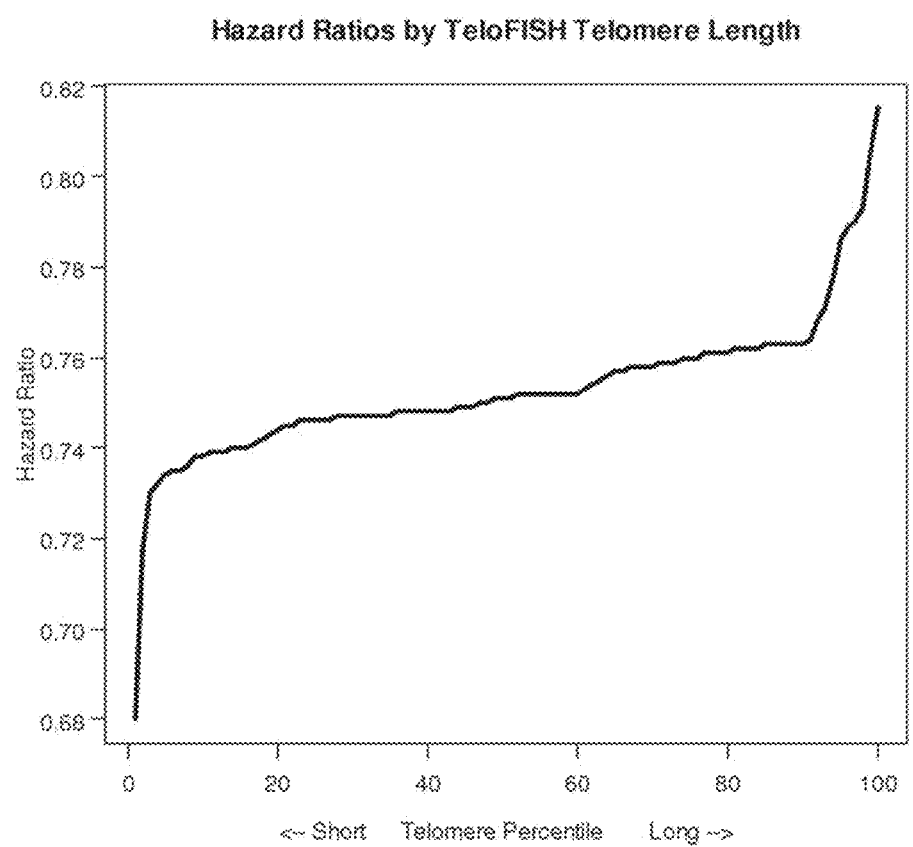
FIG. 6 depicts progression free survival (PFS) hazard ratios (HR) for patients from the Imetelstat Non-Small Cell (NSC) Lung Cancer Phase II (CP14B-012) Study plotted against patient telomere length percentiles, where the relative telomere length was determined by Telomere Fluorescent In Situ Hybridization (Telo-FISH).

Treatment effect increases in a non-linear fashion with reducing tumor telomere length (FIG. 6).

Example 4: qPCR on Formalin-Fixed, Paraffin-Embedded Samples from Imetelstat NSC Phase II (CP14B-012) Study This example demonstrates the performance of a second quantitative polymerase chain reaction for determining the relative telomere length of FFPE NSC Phase II (CP14B-012) Study tissue samples.

This Example followed all of the procedures of Example 2 with the following changes to the qPCR protocol.

Quantitative PCR (qPCR)

All quantitative PCR reactions were carried out using ABI Prism 7900 HT Sequence Detection System (Applied Biosystems, Carlsbad Calif.). One PCR was performed.

The primer sequences for telomere amplification were Telg 5'-ACA CTA AGG TTT GGG TTT GGG TTT GGG TTT GGG TTA GTG T (SEQ ID NO:4) and Telc 5'-TGT TAG GTA TCC CTA TCC CTA TCC CTA TCC CTA TCC CTA ACA (SEQ ID NO:5) (Cawthon, 2009); and those for 36B4u: 5'-CAG CAA GTG GGA AGG TGT AAT CC (SEQ ID NO:6 and 36B4d: 5'-CCC ATT CTA TCA TCA TCA ACG GGT ACA A (SEQ ID NO:7) (Cawthon, 2002).

DNA standards were also used as an assay/plate control. The sequence for the DNA standard for telomere length double stranded template was 5'-TTA GGG TTA GGG TTA GGG TTA GGG TTA GGG TTA GGG TTA GGG TTA GGG TTA GGG TTA GGG TTA GGG TTA GGG TTA GGG TTA GGG-3' (SEQ ID NO:9) and the sequence for single copy gene double stranded template was: 5'-CTT TTC AGC AAG TGG GAA GGT GTA ATC CGT CTC CAC AGA CAA GGC CAG GAC TCG TTT GTA CCC GTT GAT GAT AGA ATG GGG TAC-3' (SEQ ID NO:10) (both from Integrated DNA Technologies).

Each PCR reaction for telomere amplification on the DNA from the FFPE sample or for the oligonucleotide telomere standard was performed using 1 ng/10 μL sample (0.1 ng/μL) and a 40 μL PCR mixture containing 1.25 U Hotstart DNA Taq polymerase (BioChain), 150 nM 6-ROX fluorescent dye, 0.4×SYBR Green I nucleic acid stain (Invitrogen, Carlsbad Calif.), 50 mM KCl, 2 mM MgCl$_2$, 0.2 mM of each deoxynucleoside triphosphates (Applied Biosystems, Carlsbad, Calif.), 5 mM dithiothreitol, 1% dimethyl sulfoxide, and 15 mM Tris-HCl pH 8.0 and primer pair Telg and Telc (both at 900 nM). The higher primer concentration is preferred for the telomeric DNA when using FFPE DNA, because high concentrations of primers allow multiple annealing sites.

Amplification of the single copy 36B4 gene standard and the single copy gene in the FFPE sample was conducted using Power SYBR Green PCR Master Mix (Applied Biosystems). The 36B4 amplification was performed using 1 ng/10 μL of samples (0.1 ng/μL), 40 μL of Power SYBR Green Master Mix (Applied Biosystems, Carlsbad Calif.) and primer pair 36B4d (300 nM) and 36B4u (300 nM).

The DNA from the FFPE samples for amplification of the telomere sequence and the DNA from FFPE samples for amplification of the single copy gene were placed in separate wells on the plate. The DNA standards for amplification of telomere sequence and for amplification of single copy 36B4 gene were placed in separate wells on the same plate and all were amplified in three stages. Stage 1: 95° C. for 10 minutes to activate the DNA Taq polymerase; stage 2: 3 cycles of 15 s at 95° C., 10 s at 50° C. to generate PCR products that will act as templates for the subsequent cycles of amplification. Stage 3: 35 cycles of 15 s at 95° C., 15 s at 60° C. with signal acquisition at 60° C. Total running time was 90 minutes.

The number of cycles at stage 2 was 3 cycles in order to have proper ΔCt value ($\Delta Ct_{sample} = Ct_{telomere} - Ct_{reference}$) when using 10 ng of FFPE sample DNA in each PCR reaction. 1 ng-10 ng of FFPE Sample DNA per reaction had >94% PCR efficiency in the reproducibility studies.

Results

Figure 7A:
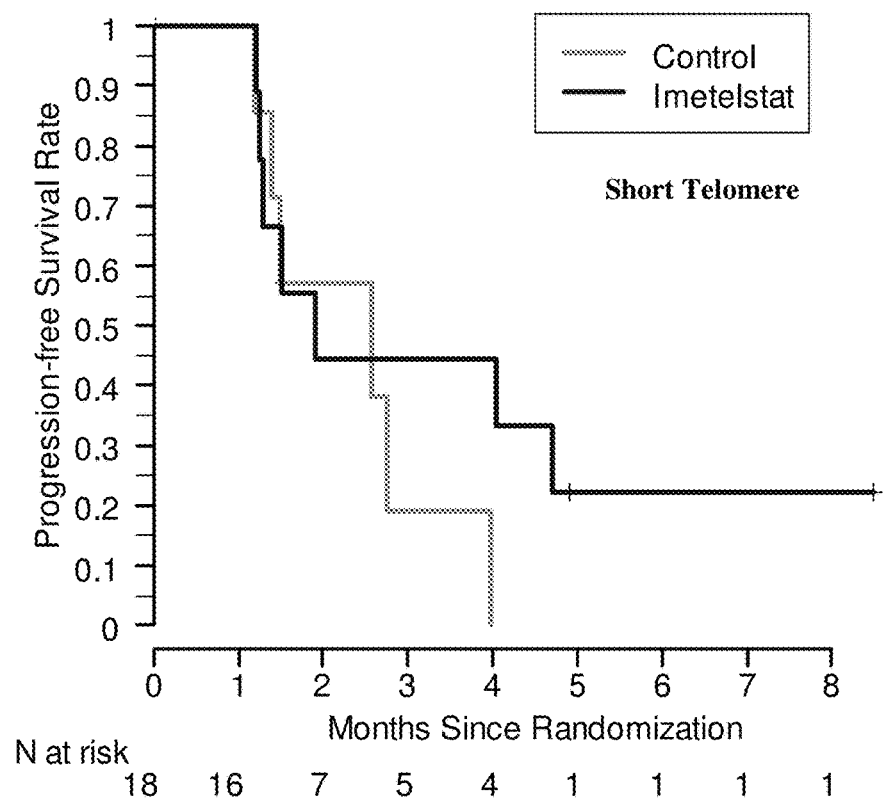
FIG. 7A depicts the progression-free survival (PFS) analysis of the short telomere subgroup (33 percentile) of the Imetelstat Non-Small Cell (NSC) Lung Cancer Phase II (CP14B-012) Study based on average telomere lengths determined using quantitative PCR (qPCR) as shown in Example 4.
Figure 7B:
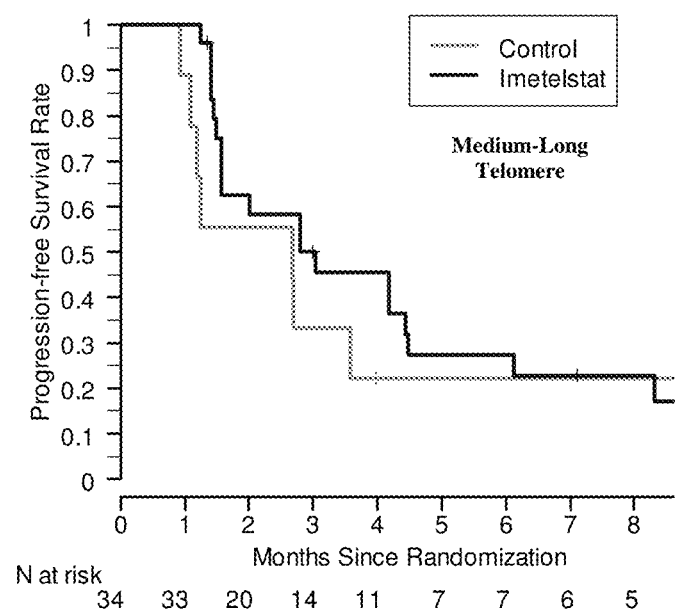
FIG. 7B depicts the progression-free survival (PFS) analysis of the medium-long telomere subgroup (longer 67% of relative telomere length) of the Imetelstat Non-Small Cell (NSC) Lung Cancer Phase II (CP14B-012) Study based on average telomere lengths determined using quantitative PCR (qPCR) as shown in Example 4.

Analysis of progression-free survival in telomere length subgroups obtained by qPCR indicated patients with short telomeres who were treated with Imetelstat were significantly more responsive compared to controls than patients with medium-long telomeres (FIGS. 7A and 7B).

18 out of the 52 samples (35%) had short telomeres (FIG. 7A). For these, the progression-free survival analysis indicated the following: events/N were 13/18 (FIG. 7A); the control median (95% CI) was 2.57 (1.18, NA), and the Imetelstat median (95% CI) was 1.91 (1.22, NA) (FIG. 7A); the log rank P-value was 0.325, and the Hazard ratio (95% CI) was 0.55 (0.17, 1.84) (FIG. 7A).

34 out of the 52 samples (65%) had medium-long telomeres (FIG. 7B). For these, the progression-free survival analysis indicated the following: events/N were 26/34 (FIG. 7B); the control median (95% CI) was 2.66 (0.92, NA), and the Imetelstat median (95% CI) was 3.03 (1.58, 4.47) (FIG. 7B); the log rank P-value was 0.309, and the Hazard ratio (95% CI) was 0.65 (0.27, 1.56) (FIG. 7B).

The examples, which are intended to be purely exemplary of the invention and should therefore not be considered to limit the invention in any way, also describe and detail aspects and embodiments of the invention discussed above. The foregoing examples and detailed description are offered by way of illustration and not by way of limitation. All publications, patent applications, and patents cited in this specification are herein incorporated by reference as if each individual publication, patent application, or patent were specifically and individually indicated to be incorporated by reference. In particular, all publications cited herein are expressly incorporated herein by reference for the purpose of describing and disclosing compositions and methodologies which might be used in connection with the invention. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

The invention claimed is:

1. A method of detecting a relative telomere length in a sample from an individual diagnosed with or suspected of having a solid tumor cancer, the method comprising:
obtaining a formalin fixed paraffin embedded (FFPE) biological sample comprising cancer cells of a solid tumor from the individual;
analyzing the relative length of telomeric nucleic acids in cancer cells of the FFPE biological sample via quantitative PCR (qPCR) or telomere fluorescent in situ hybridization (telo-FISH) and determining whether the average relative telomere length in the cancer cells present in the FFPE biological sample from the individual is in the 50$^{th}$ percentile or less of a relative telomere length range determined from one or more known standards selected from a telomere length range established from a plurality of naturally occurring tumors from a plurality of individuals diagnosed with the cancer and characterized cell lines.

2. The method of claim 1, wherein the cancer is selected from lung cancer, breast cancer, liver cancer, ovarian cancer, gastric cancer, gastrointestinal cancer, gallbladder cancer, bladder cancer, glioblastoma, a sarcoma, melanoma, colorectal cancer and pancreatic cancer.

3. The method of claim 1, wherein relative telomere length is determined by qPCR.

4. The method of claim 1, wherein said one or more known standards are characterized cell lines.

5. The method of claim 1, wherein said one or more known standards is from a plurality of naturally occurring tumors from a plurality of individuals.

6. The method of claim 2, wherein the cancer is non-small cell lung cancer.

7. The method of claim 1 wherein the individual is a human.

8. The method of claim 4, wherein the characterized cell lines are selected from the group consisting of: M14 cells, A549 cells, SK-5 cells, and Ovcar5 cells.

9. The method of claim 4, wherein the characterized cell lines are selected from cell lines representative of the cancer cells present in the FFPE biological sample from the individual.

10. The method of claim 9, wherein the characterized cell lines are non-small cell lung cancer cell lines, hepatocellular cell lines, or ovarian cell lines.

11. The method of claim 5, wherein said cancer cells from the plurality of naturally occurring tumors are of the same type as the cancer cells present in the FFPE biological sample from the individual.

12. The method of claim 1, wherein the average relative telomere length in the cancer cells present in the FFPE biological sample is determined to be in the 40th percentile, 35th percentile, 30th percentile, 25th percentile, 20th percentile, 15th percentile, 10th percentile, or 5th percentile or less of the relative telomere length range determined from the one or more known standards.

13. The method of claim 1, wherein the relative telomere length is determined by telo-FISH.

14. The method of claim 13, wherein the method further comprises deparaffinization of the FFPE biological sample.

15. The method of claim 3, further comprising extracting the telomeric nucleic acids from the FFPE biological sample before determining relative telomere length.

* * * * *

SEQUENCE LISTING

<160> NUMBER OF SEQ ID NOS: 10

<210> SEQ ID NO 1
<211> LENGTH: 554
<212> TYPE: RNA
<213> ORGANISM: Homo sapiens

<400> SEQUENCE: 1

```
ggguugcgga ggugggccu gggaggggug guggccauuu uuugucuaac ccuaacugag      60
aagggcguag gcgccgugcu uuugcucccc gcgcgcuguu uuucucgcug acuuucagcg     120
ggcggaaaag ccucggccug ccgccuucca ccguucauuc uagagcaaac aaaaaauguc     180
agcugcuggc ccguucgccu cccgggggacc ugcggcgggu cgccugccca gcccccgaac    240
cccgccugga gccgcggucg gcccggggcu ucuccggagg cacccacugc caccgcgaag     300
aguugggcuc ugucagccgc gggucucucg ggggcgaggg cgagguucac cguuucaggc     360
cgcaggaaga ggaacggagc gagucccgcc gcggcgcgau ucccugagcu gugggacgug     420
cacccaggac ucggcucaca caugcaguuc gcuuuccugu ugguggggg aacgccgauc      480 gugcgcaucc gucaccccuc gccggcagug ggggcuugug aacccccaaa ccugacugac     540
ugggccagug ugcu                                                      554
```

<210> SEQ ID NO 2
<211> LENGTH: 11
<212> TYPE: RNA
<213> ORGANISM: Artificial sequence
<220> FEATURE:
<223> OTHER INFORMATION: hTR template inhibitor

<400> SEQUENCE: 2

```
cuaacccuaa c                                                          11
```

<210> SEQ ID NO 3
<211> LENGTH: 13
<212> TYPE: DNA
<213> ORGANISM: Artificial sequence
<220> FEATURE:
<223> OTHER INFORMATION: hTR template inhibitor

<400> SEQUENCE: 3

```
tagggttaga caa                                                        13
```

<210> SEQ ID NO 4
<211> LENGTH: 40
<212> TYPE: DNA
<213> ORGANISM: Artificial sequence
<220> FEATURE:
<223> OTHER INFORMATION: primer for telomere amplification

<400> SEQUENCE: 4

```
acactaaggt ttgggtttgg gtttgggttt gggttagtgt                           40
```

<210> SEQ ID NO 5
<211> LENGTH: 42
<212> TYPE: DNA
<213> ORGANISM: Artificial sequence
<220> FEATURE:
<223> OTHER INFORMATION: primer for telomere amplification

<400> SEQUENCE: 5

```
tgttaggtat ccctatccct atccctatcc ctatccctaa ca                        42
```

```
<210> SEQ ID NO 6
<211> LENGTH: 23
<212> TYPE: DNA
<213> ORGANISM: Artificial sequence
<220> FEATURE:
<223> OTHER INFORMATION: primer for telomere amplification

<400> SEQUENCE: 6
cagcaagtgg gaaggtgtaa tcc                                              23

<210> SEQ ID NO 7
<211> LENGTH: 28
<212> TYPE: DNA
<213> ORGANISM: Artificial sequence
<220> FEATURE:
<223> OTHER INFORMATION: primer for telomere amplification

<400> SEQUENCE: 7
cccattctat catcatcaac gggtacaa                                         28

<210> SEQ ID NO 8
<211> LENGTH: 18
<212> TYPE: DNA
<213> ORGANISM: Artificial sequence
<220> FEATURE:
<223> OTHER INFORMATION: telomere probe

<400> SEQUENCE: 8
ccctaaccct aaccctaa                                                    18

<210> SEQ ID NO 9
<211> LENGTH: 84
<212> TYPE: DNA
<213> ORGANISM: Artificial sequence
<220> FEATURE:
<223> OTHER INFORMATION: standard for telomere length double stranded
      template

<400> SEQUENCE: 9
ttagggttag ggttagggtt agggttaggg ttagggttag ggttagggtt agggttaggg      60
ttagggttag ggttagggtt aggg                                             84

<210> SEQ ID NO 10
<211> LENGTH: 84
<212> TYPE: DNA
<213> ORGANISM: Artificial sequence
<220> FEATURE:
<223> OTHER INFORMATION: standard for single copy gene double stranded
      template

<400> SEQUENCE: 10
cttttcagca agtgggaagg tgtaatccgt ctccacagac aaggccagga ctcgtttgta      60
cccgttgatg atagaatggg gtac                                             84
```